US009901285B2

(12) United States Patent
Majumdar et al.

(10) Patent No.: US 9,901,285 B2
(45) Date of Patent: *Feb. 27, 2018

(54) SYSTEMS AND METHODS USING NUCLEAR MAGNETIC RESONANCE (NMR) SPECTROSCOPY TO EVALUATE PAIN AND DEGENERATIVE PROPERTIES OF TISSUE

(71) Applicant: THE REGENTS OF THE UNIVERSITY OF CALIFORNIA, Oakland, CA (US)

(72) Inventors: Sharmila Majumdar, Alameda, CA (US); John Kurhanewicz, South San Francisco, CA (US); Jeffrey C. Lotz, San Mateo, CA (US); David S. Bradford, Sausalito, CA (US); Kayvan Keshari, Stockton, CA (US)

(73) Assignee: THE REGENTS OF THE UNIVERSITY OF CALIFORNIA, Oakland, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 13/680,612

(22) Filed: Nov. 19, 2012

(65) Prior Publication Data
US 2013/0144155 A1 Jun. 6, 2013

Related U.S. Application Data

(63) Continuation of application No. 11/829,847, filed on Jul. 27, 2007, now Pat. No. 8,344,728, which is a
(Continued)

(51) Int. Cl.
*A61B 5/00* (2006.01)
*A61B 5/055* (2006.01)
(Continued)

(52) U.S. Cl.
CPC ............ *A61B 5/055* (2013.01); *A61B 5/4824* (2013.01); *G01N 24/08* (2013.01); *G01R 33/483* (2013.01);
(Continued)

(58) Field of Classification Search
None
See application file for complete search history.

(56) References Cited

U.S. PATENT DOCUMENTS

| 5,068,098 A | 11/1991 | Schweighardt et al. |
| 5,270,651 A | 12/1993 | Wehrli et al. |

(Continued)

FOREIGN PATENT DOCUMENTS

| JP | S63-204143 A | 8/1988 |
| JP | H05-509162 T | 12/1993 |

(Continued)

OTHER PUBLICATIONS

M Petrantonaki, et al., "MRI Technique of the Examination of Trabecular Bone Structure," Current Imaging Review 2005, 1: pp. 35-41.
(Continued)

*Primary Examiner* — Amanda Lauritzen Moher
(74) *Attorney, Agent, or Firm* — O'Banion & Ritchey LLP; John P. O'Banion

(57) ABSTRACT

NMR spectroscopy is performed on intervertebral disc tissue. Extent of degeneration is determined based on the NMR spectroscopy. Correlation between NMR spectral regions and at least one of tissue degeneration and pain are made. Accordingly, NMR spectroscopy is used to determine location and/or extent of at least one of degeneration or pain associated with a region of tissue, such as for example in particular disc degeneration, or discogenic pain. NMR spectral peak ratios, such as between N-Acetyl/cho and cho/carb, are readily acquired and analyzed to predict degree of tissue degeneration and/or pain for: tissue samples using HR-MAS spectroscopy; and larger portions of anatomy such as joint segments such as a spine, using clinical 3T MRI systems with surface head or knee coils; and tissue regions such as discs within spines of living patients using 3T MRI systems
(Continued)

with a surface spine coil, thus providing a completely non-invasive diagnostic toolset and method to image and localize degeneration and/or pain.

15 Claims, 14 Drawing Sheets

Related U.S. Application Data continuation-in-part of application No. PCT/US2006/003036, filed on Jan. 30, 2006.

(60) Provisional application No. 60/737,110, filed on Nov. 15, 2005, provisional application No. 60/648,241, filed on Jan. 28, 2005.

(51) Int. Cl.
*G01N 24/08* (2006.01)
*G01R 33/483* (2006.01)
*G01R 33/465* (2006.01)
*G01R 33/485* (2006.01)

(52) U.S. Cl.
CPC ........... *A61B 5/4514* (2013.01); *A61B 5/4528* (2013.01); *G01R 33/465* (2013.01); *G01R 33/485* (2013.01)

(56) References Cited

U.S. PATENT DOCUMENTS

| | | | |
|---|---|---|---|
| 5,844,097 | A | 12/1998 | Cameron, Sr. et al. |
| 6,018,675 | A | 1/2000 | Apkarian et al. |
| 6,278,891 | B1* | 8/2001 | Reiderman et al. ......... 600/410 |
| 6,686,348 | B2 | 2/2004 | De Nanteuil et al. |
| 7,676,254 | B2* | 3/2010 | Siddall et al. ............. 600/410 |
| 8,344,728 | B2* | 1/2013 | Majumdar et al. .......... 324/309 |
| 8,761,860 | B2* | 6/2014 | Peacock et al. ............ 600/410 |
| 8,825,131 | B2* | 9/2014 | Peacock et al. ............ 600/410 |
| 8,965,094 | B2* | 2/2015 | Peacock, III ...... G01R 33/4625 128/922 |
| 9,280,718 | B2* | 3/2016 | Claude .................. A61B 5/055 |
| 9,392,959 | B2* | 7/2016 | Peacock, III .......... A61B 5/055 |
| 9,724,013 | B2* | 8/2017 | Peacock, III .......... A61B 5/055 |
| 2001/0003423 | A1 | 6/2001 | Wald |
| 2002/0037251 | A1 | 3/2002 | Driehuys |
| 2004/0006376 | A1 | 1/2004 | Falci |
| 2004/0214348 | A1 | 10/2004 | Nicholson et al. |
| 2005/0020905 | A1 | 1/2005 | Siddall et al. |

FOREIGN PATENT DOCUMENTS

| | | |
|---|---|---|
| JP | H06-503418 T | 4/1994 |
| JP | 2003524490 A | 8/2003 |
| JP | 2004526130 A | 8/2004 |
| JP | 2004528559 A | 9/2004 |
| WO | 2004099808 A1 | 11/2004 |

OTHER PUBLICATIONS

JC Ford and FW Wehrli, "In vivo Quantitative Characterization of Trabecular Bone by NMR Interferometry and Localized Proton Spectroscopy," Magnetic Resonance in Medicine 1991; 17: pp. 543-551.
J Schiller et al., "Evaluation of Cartilage Composition and Degradation by High-Resolution Magic-Angle Spinning Nuclear Magnetic Resonance", Methods in Molecular Medicine 2004; 101: pp. 267-285.
Keshari, K. et al.—"Characterization of Intervertebral Disc Degeneration by High-Resolution Magic Angle Spinning (HR-MAS) Spectroscopy"—Magnetic Resonance in Medicine—vol. 53, 2005, pp. 519-527.
European Patent Office, Communication pursuant to Article 94(3) EPC (office action) dated May 3, 2011 for EPO application No. 06 374 001.8-2319, with claims examined, counterpart to PCT/US2006/03036 claiming priority to U.S. Appl. No. 60/731,110 and U.S. Appl. No. 60/648,241 and related to U.S. Appl. No. 11/829,847, pp. 1-8.
European Patent Office, Extended European Supplementary Search Report (pp. 1-7) dated May 20, 2010 for Counterpart European patent application No. EP 06 73 4001.8 and claims searched (pp. 8-10) pp. 1-10.
Haro, H. et al.—"Matrix metalloproteinase-7-dependent release of tumor necrosis factor in a model of herniated disc resorption"—Jour. of Clinical Inv., vol. 105, No. 2, Jan. 2000, pp. 143-150.
Mow, V.C. et al.—"Basic Orthopaedic Biomechanics—Chapter 10—Biomechanics of the Human Spine"—1997, pp. 353-393.
Thompson, J. et al.—"Preliminary Evaluation of a Scheme for Grading the Gross Morphology of the Human Intervertebral Disc"—Spine, vol. 15, 1990, pp. 411-415.
Iatridis, J. et al.—"Alterations in the Mechanical Behavior of the Human Lumbar Nucleas Pulposus with Degeneration and Aging"—Jour of Ortho Research, vol. 15, 1997, pp. 318-322.
Beall, et al.—"NMR Data Handbook for Biomedical Applications"—New York, Pergamon Press, 1984, 11 pages.
Bottomley, P. et al.—"A review of normal tissue hydrogen NMR relaxation times and relaxation mechanisms from 1-100 MHz: Dependence on tissue type, NMR frequency, temperature, species, excision and age"—Med. Phys., vol. 11, No. 4, Jul./Aug. 1984, pp. 425-448.
Lyons, G. et al.—"Biochemical Changes in Intervertebral Disc Degeneration"—Biochimica Biophys Acta, vol. 673, 1981, pp. 443-453.
Maroudas, A.—"The Biology of the Intervertebral Disc"'In: Ghosh, P. et. The Biology of the Intervertebral Disc, vol. II, Chapter 9, 1988.
Pearce, R. et al.—"Degeneration and the Chemical Composition of the Human Lumbar Intervertebral Disc"—Jour. of Ortho. Research, vol. 5, 1987, pp. 198-205.
Tertti, M. et al.—"Disc Degeneration in Magnetic Resonance Imaging: A Comparative Biochemical, Histologic, and Radiologic Study in Cadaver Spines"—Spine, 1991, pp. 629-634.
Chiu, E. et al.—"Magnetic Resonance Imaging Measurement of Relaxation and Water Diffusion in the Human Lumbar Intervertebral Disc Under Compression in Vitro"—Spine, vol. 26, No. 19, 2001, pp. E437-E444.
Gundry, C. et al.—"Magnetic Resonance Imaging of the Musculoskeletal System, Part 8. The Spine, Section 1", Clinical Ortho. and Related Research, vol. 338, May 1997, pp. 275-287.
Gunzburg, R. et al.—"A Cadaveric Study Comparing Discography, Magnetic Resonance Imaging, Histology, and Mechanical Behavior of the Human Lumbar Disc"—Spine, 1991, pp. 417-423.
Modic, M. et al.—"Magnetic Resonance Imaging of Intervertebral Disk Disease"—Radiology, vol. 152, 1984, pp. 103-111.
Modic, M. et al.—"Lumbar Herniated Disk Disease and Canal Stenosis: Prospective Evaluation by Surface Coil MR, CT, and Myelography"—AJR, vol. 147, Oct. 1986, pp. 757-765.
Modic, M. et al.—"Imaging of Degenerative Disk Disease"—Radiology, vol. 168, 1988, pp. 177-186.
Sether, L. et al.—"Intervertebral Disk: Normal Age-related Changes in MR Signal Intensity"—Radiology, vol. 177, 1990, pp. 385-388.
Nieminen, M. et al.—"Spatial Assessment of Articular Cartilage Proteoglycans with Gd-DTPA-Enhanced T1 Imaging"—Mag. Res. in Med., vol. 48, 2002, pp. 640-648.
Mosher, T. et al.—"Human Articular Cartilage: Influence of Aging and Early Symptomatic Degeneration on the Spatial Variation of T2-Preliminary Findings at 3 T1"—Radiology, vol. 214, 2000, pp. 259-266.
Burstein, D. et al.—"Diffusion of Small Solutes in Cartilage as Measured by Nuclear Magnetic Resonance (NMR) Spectroscopy and Imaging"—Jour. of Ortho. Res., vol. 11, 1993, pp. 465-478.
Abdulkarim, J. et al.—"Magnetic Resonance Imaging of the Cervical Spine: Frequency of Degenerative Changes in the Intervertebral Disc With Relation to Age"—Clinical Radiology, vol. 58, 2003, pp. 980-984.

(56) References Cited

OTHER PUBLICATIONS

Swanson, M. et al.—"Proton HR-MAS Spectroscopy and Quantitative Pathologic Analysis of MRI/3D-MRSI-Targeted Postsurgical Prostate Tissues"—Mag. Resonance in Med., vol. 54, 2003, pp. 944-954.

Schiller, J. et al.—"1H and 13C HR-MAS NMR investigations on native and enzymatically digested bovine nasal cartilage"—Mag. Resonance Mater. in Phy., Biol., and Med., vol. 13, 2001, pp. 19-27.

Carr, H. et al.—"Effects of Diffusion on Free Precession in Nuclear Magnetic Resonance Experiments"—Phys. Review, vol. 94, No. 3, May 1, 1954, pp. 630-638.

Kupce, E.—"Applications of Adiabatic Pulses in Biomolecular Nuclear Magnetic Resonance"—Methods in Enzymology, vol. 338, 2001, pp. 82-111.

Mucci, A. et al.—"1H and 13C nuclear magnetic resonance identification and characterization of components of chondroitin sulfates of various origin"—Carbohydrate Polymers, vol. 41, 2003, pp. 37-45.

Groupille, P. et al.—"Matrix Metalloproteinases: The Clue to Intervertebral Disc Degeneration?"—Spine, vol. 23, No. 14, Jul. 1998, pp. 1612-1626.

Kang, J. et al.—"Towards a Biochemical Understanding of Human Intervertebral Disc Degeneration and Herniation: Contributions of Nitric Oxide, Interleukins, Prostaglandin E2, and Matrix Metalloproteinases"—spine, vol. 22, No. 10, May 15, 1997, pp. 1065-1073.

Weiler, C. et al.—"2002 SSE Award Competition in Basic Science: Expression of major matrix metalloproteinases is associated with intervertebral disc degradation and resorption"—Eur. Spine Jour., vol. 11, 2002, pp. 308-320.

Urban, J. et al.—"The Nucleus of the Intervertebral Disc from Development to Degeneration"—American Zoologist, vol. 40, No. 1, Feb. 2000, pp. 53-61.

Weidenbaum, M. et al.—"Correlating Magnetic Resonance Imaging with the Biochemical Content of the Normal Human Intervertebral Disc"—Jour. of Ortho. Research, vol. 10, 1992, pp. 552-561.

Boos, N. et al.—"Quantitative MR Imaging of Lumbar Intervertebral Disks and Vertebral Bodies: Influence of Diurnal Water Content Variations"—Radiology, vol. 188, 1993, pp. 351-354.

Boos, N. et al.—"Quantitative MR Imaging of Lumbar Intervertebral Discs and Vertebral Bodies: Methodology, Reproducibility, and Preliminary Results"—Mag. Res. Imaging, vol. 12, No. 4, 1994, pp. 577-587.

C-T. Chung et al. Single photon emission computed tomography (SPECT) for low back pain induced by extension with no root sign. J. Chin. Med. Assoc. vol. 67, pp. 349-354 (2004).

J.O. Lusins et al. SPECT and lumbar MRI in back pain with emphasis on changes in end plates in association with disc degeneration (abstract). J. Neuroimaging, vol. 8, No. 2, pp. 78-82 (1998).

M. McDonald et al. Use of computer tomography—single-photon emission computed tomography fusion for diagnosing painful facet arthropathy. Neurosurg. Focus, vol. 22, No. 1, E2 (2007).

D.S. Mulconrey et al. Interobserver reliability in the interpretation of diagnostic lumbar MRI and nuclear imaging. The Spine Journal, vol. 6, pp. 177-184 (2006).

Keshari, K. et al.—Poster and Abstract—"Identification of Chondroitin Sulfate as a Marker for Human Intervertebral Disc Degeneration Using Proton High Resolution Magic Angle Spinning (HR-MAS) Spectroscopy"—The 44th ENC, Mar. 30-Apr. 4, 2003, 22 pages.

Majumdar, S.—Abstract—"Spectroscopic Markers of Disc Degeneration"—downloaded from CRISP website Nov. 23, 2004, 2 pages.

Keshari, K. et al.—"Correlation of HR-MAS Spectroscopy Derived Metabolite Concentrations With Collagen and Proteoglycan Levels and Thompson Grade in the Degenerative Disc"—Spine, vol. 30, No. 23, Dec. 1, 2005, pp. 2683-2688.

European Patent Office, Office Action dated Apr. 17, 2012 (pp. 1-5) with claims (pp. 6-10), EP Patent Application No. 06 734 001.8, counterpart to PCT/US2006/003036, claiming priority U.S. Appl. No. 60/648,241 and U.S. Appl. No. 60/737,110, pp. 1-10.

Japanese Patent Office, Office Action dated Jun. 14, 2011, Patent Application No. 2007-553286, English translation (pp. 1-3), original Japanese Language copy ( pp. 4-5), with claims (pp. 6-16), counterpart to PCT/US2006/003036, claiming priority to U.S. Appl. No. 60/737,110 and U.S. Appl. No. 60/648,241.

The State Intellectual Property Office of the People's Republic of China, Decision of Rejection dated Jul. 26, 2011, Patent Application No. 200680009431.8, English translation (pp. 1-5), original Chinese Language copy (pp. 6-8), with claims (pp. 9-11), counterpart to PCT/US2006/003036, claiming priority to U.S. Appl. No. 60/737,110 and U.S. Appl. No. 60/648,241.

Japanese Patent Office, Office Action dated Jun. 12, 2012 (pp. 1-3) with English-language translation (pp. 4-7) and claims examined (pp. 8-11), related JP Patent Application No. 2007-553286, counterpart to PCT/US2006/003036, claiming priority U.S. Appl. No. 60/648,241 and U.S. Appl. No. 60/737,110, pp. 1-11. The cited reference, US2005/0020905 (now U.S. Pat. No. 7,676,254), is the was considered by the U.S. Examiner in the Office Action for this case (U.S. Appl. No. 11/829,847) dated Nov. 10, 2010.

Boos, Norbert et al., "Quantitative Magnetic Resonance Imaging of the Lumbar Spine—Potential for Investigations of Water Content and Biochemical Composition", Spine vol. 20, No. 21, pp. 2358-2365, 1995.

Pfirrmann, Christian W. A. et al., "Magnetic Resonance Classification of Lumbar Intervertebral Disc Degeneration", Spine vol. 26, No. 17, pp. 1873-1878, 2001.

Urban, Jill P.G. et al., "Nutrition of the Intervertebral Disc", SPINE vol. 29, No. 23, pp. 2700-2709, 2004.

* cited by examiner

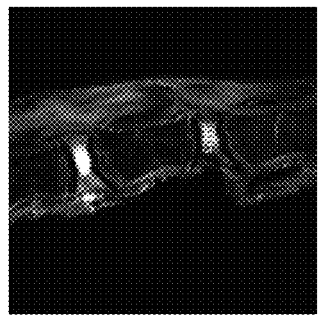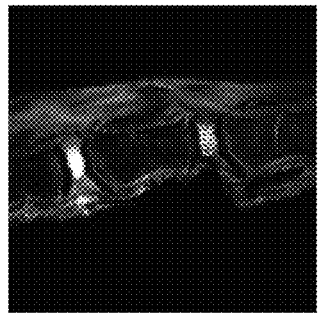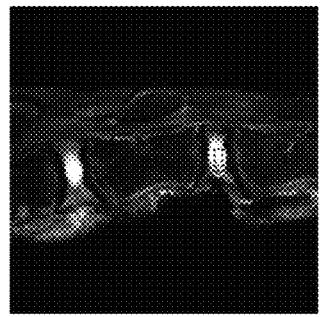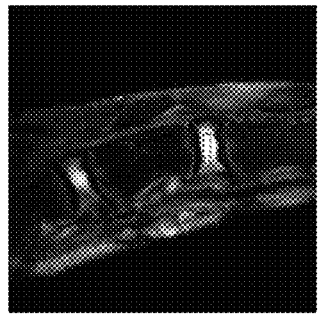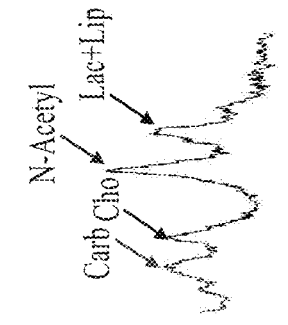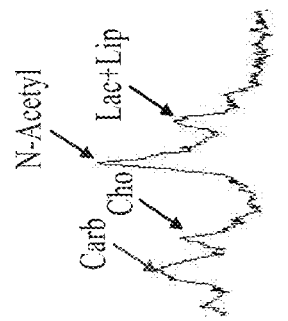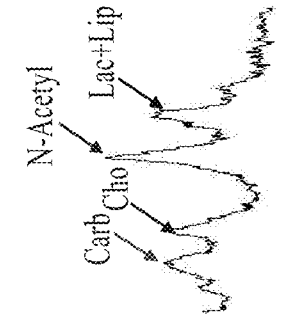

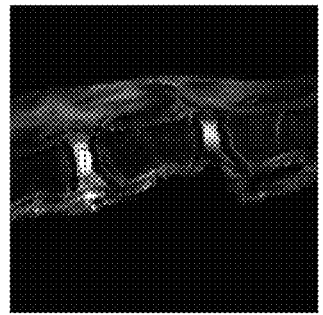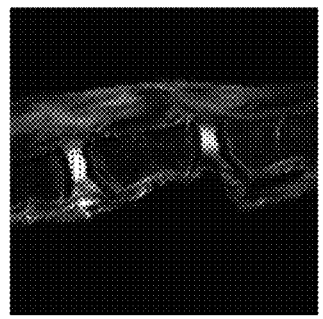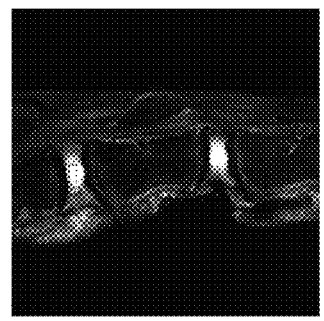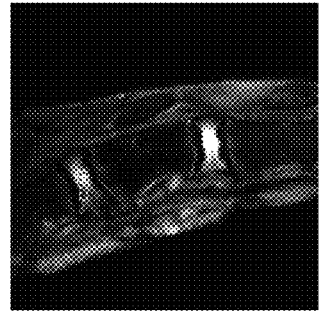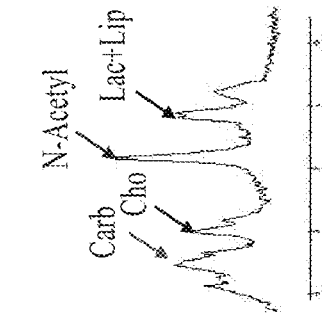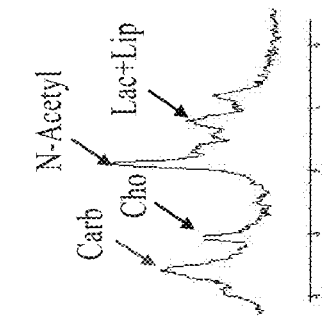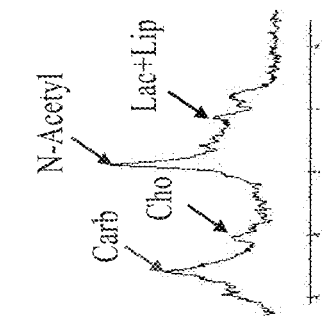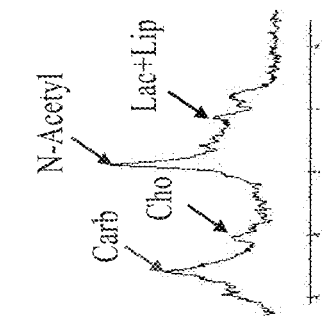

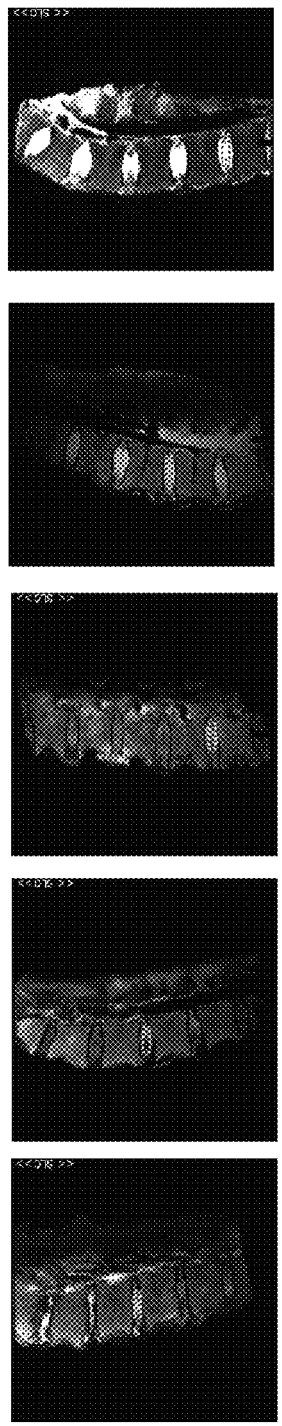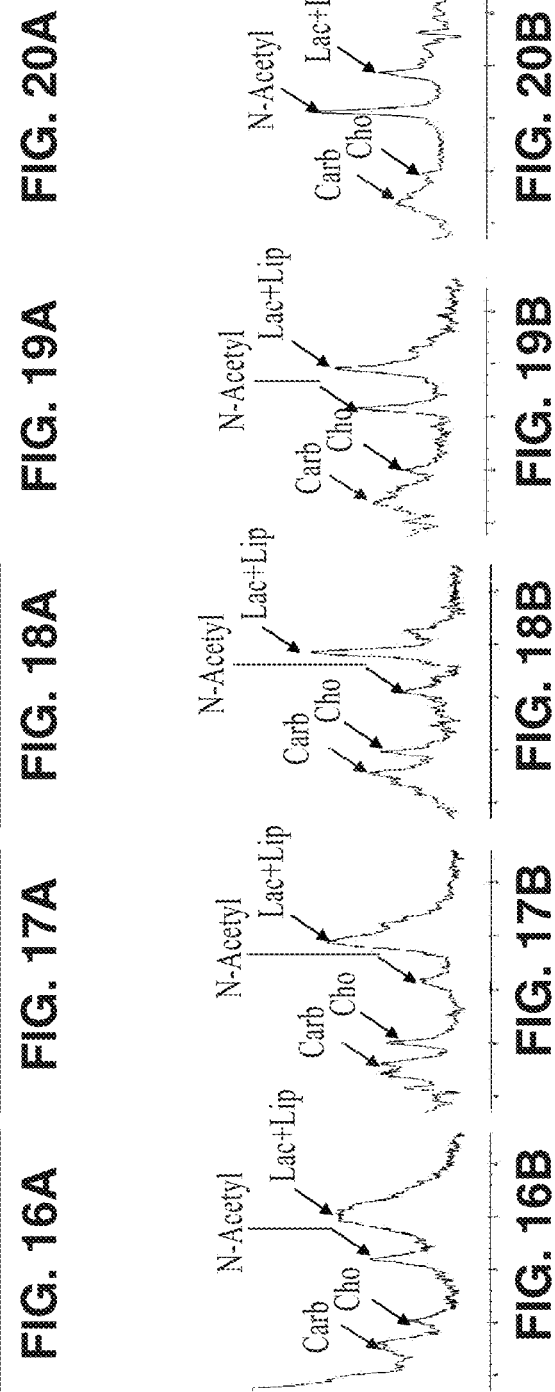
FIG. 16A FIG. 17A FIG. 18A FIG. 19A FIG. 20A
FIG. 16B FIG. 17B FIG. 18B FIG. 19B FIG. 20B

SYSTEMS AND METHODS USING NUCLEAR MAGNETIC RESONANCE (NMR) SPECTROSCOPY TO EVALUATE PAIN AND DEGENERATIVE PROPERTIES OF TISSUE

CROSS-REFERENCE TO RELATED APPLICATIONS

This application is a continuation of U.S. patent application Ser. No. 11/829,847 filed on Jul. 27, 2007, now U.S. Pat. No. 8,344,728, incorporated herein by reference in its entirety, which is a 35 U.S.C. § 111(a) continuation-in-part of PCT international application serial number PCT/US2006/003036 filed on Jan. 30, 2006, incorporated herein by reference in its entirety, which is a nonprovisional of U.S. provisional patent application Ser. No. 60/737,110, filed on Nov. 15, 2005, incorporated herein by reference in its entirety, and which is a nonprovisional of U.S. provisional patent application Ser. No. 60/648,241, filed on Jan. 28, 2005, incorporated herein by reference in its entirety. Priority is claimed to each of the foregoing applications.

This application is also related to PCT International Publication No. WO 2006/081471 published on Aug. 3, 2006 and republished on Aug. 23, 2007, incorporated herein by reference in its entirety. This application is also related to U.S. Patent Application Publication No. US-2008-0039710-A1 published on Feb. 14, 2008, incorporated herein by referenced in its entirety.

STATEMENT REGARDING FEDERALLY SPONSORED RESEARCH OR DEVELOPMENT

This invention was made with Government support under Grant Nos. R01-AG17762 and R21-AR51048 awarded by National Institutes of Health. The Government has certain rights in this invention.

INCORPORATION-BY-REFERENCE OF MATERIAL SUBMITTED ON A COMPACT DISC

Not Applicable

NOTICE OF MATERIAL SUBJECT TO COPYRIGHT PROTECTION

A portion of the material in this patent document is subject to copyright protection under the copyright laws of the United States and of other countries. The owner of the copyright rights has no objection to the facsimile reproduction by anyone of the patent document or the patent disclosure, as it appears in the United States Patent and Trademark Office publicly available file or records, but otherwise reserves all copyright rights whatsoever. The copyright owner does not hereby waive any of its rights to have this patent document maintained in secrecy, including without limitation its rights pursuant to 37 C.F.R. §1.14.

BACKGROUND OF THE INVENTION

1. Field of the Invention

This invention pertains generally to imaging of tissues associated with skeletal joints, and more particularly to identifying and/or characterizing medical conditions associated with skeletal joints, pain, or both. Still more specifically, it relates to using nuclear magnetic resonance (NMR) spectroscopy to identify, localize, and/or characterize chemical, molecular, structural, or other signatures related to medical conditions in tissues, such as degradation or pain associated with skeletal joints (for example spine).

2. Description of Related Art

Intervertebral disc degeneration (IVDD) is a leading cause of lumbar spine related lower back pain, a common medical problem that affects 60 to 80% of aging Americans. The intervertebral disc is a flexible fibrocartilaginous structure that supports forces and facilitates spinal movement. Healthy discs consist of three specific tissue components: 1) the annulus fibrosus, a collagenous region tightly packed circumferentially around the periphery of the disc which allows for pliability; 2) the nucleus pulposus, a hydrated, proteoglycan gel located at the center of the disc, which when compressed expands radially and braces the annulus fibrosus to maintain stiffness and prevents the annulus from buckling under compression; and 3) a cartilaginous endplate that separates the nucleus from the adjacent vertebral bone.

Disc degeneration is characterized by a complex series of physical and chemical degradative processes. The extent or severity of IVDD is most commonly described clinically using the Thompson Grading Scale, where following a set of parameters, a x-ray radiographic inspection of the disc is conducted and the gross morphology is used to determine the extent of degeneration. One research group has concluded that changes to the mechanical properties of the intervertebral disc suggest a shift from a "fluid like" behavior to a more "solid like" behavior with degeneration. Fixed charge density (FCD) and the biochemical environment of the surrounding water have also been shown to greatly influence degeneration; as highly charged proteoglycans attract water and cause the tissue to swell, disc pressurization and spinal load support are directly affected. Differences in the Thompson Grade are reflected by changes in the concentrations of constituents such as collagen and proteoglycans in both the annulus and nucleus. It has been proposed that biochemical degradation, upregulation of genes associated with collagen matrix degradation, and the cumulative effect of mechanical loading, all stimulate the degenerative disc process.

Identification and characterization of disc degeneration thus involves a wide array of technological developments and efforts over many years. Yet, an adequate, repeatable, non-invasive system and method to characterize factors related to pain, pain generation, or disc degeneration has yet to be provided as a useful medical tool.

It is also well appreciated in current medical practice that pain is a remarkably difficult phenomenon to diagnose and localize. This is in particular the case with respect to skeletal joint pain, and in particular back pain. Whereas certain targeted pain relief therapies may be made available, such as directed energy sources to locally ablate painful nociceptive nerves, the indentification and localization of where to treat is a critical pacing item that often falls well short of providing the requisite specificity. As a result, the ability to successfully target such therapies in overall pain management is extremely challenging at best.

Degenerative disc disease, while a predominant cause of debilitating back pain, is however only one example of medical conditions in dire need for better tools and methods to characterize and localize the condition in order to appropriately direct therapies. Chronic back pain, for example, may result from several underlying root causes. These causes include, for example, vertebral compression fractures, degenerative disc disease, and disc herniation. In addition, other joint pain, such as of the spine or other skeletal joints (e.g. knuckles, ankles, knees, hips, shoulders, wrists, elbows) may also be the result of many different underlying causes (or combinations of them), and may also be very difficult to localize sufficiently to direct localized therapies. Pain associated with any or all of these joints may be located at the connective or cushioning tissue of the joint itself (e.g. the disc for spinal joints), or within the bone, or at transitional areas (e.g. the end-plates of vertebral bodies bordering discs).

A substantial need exists for improved non-invasive tools and methods for identifying and characterizing the degradation of tissues in the body. This is in particular the case with respect to skeletal joints, in particular intervertebral joints of the spine, and further in particular in and around the intervertebral discs themselves.

A substantial need also exists for improved non-invasive tools and methods for identifying, characterizing, and/or localizing pain within the body. This is also in particular the case with respect to skeletal joints, in particular intervertebral joints of the spine, and further in particular in and around the intervertebral discs themselves.

BRIEF SUMMARY OF THE INVENTION

One aspect of the present disclosure provides a medical diagnostic system with a non-invasive imaging modality that is adapted to provide useful information that is indicative of a degree of a property of a region of tissue based upon a chemical signature of a factor associated with that property.

Spectra obtained using the NMR spectroscopic method are very similar for samples taken from annular and nuclear regions of discs. Visually apparent changes are observed in the spectra of the annular and nuclear samples from discs with increasing Thompson grade. Area ratios of the N-Acetyl to choline regions and the choline to carbohydrate regions of the spectra allow for discrimination between discs of increasing Thompson grade with minimal overlap of individual ratios.

According to one mode of this aspect, the property is associated with pain.

According to another mode of this aspect, the property is associated with tissue degeneration.

According to another mode of this aspect, the system provides useful information that is indicative of a property associated with a skeletal joint.

According to another mode of this aspect, the system provides useful information that is indicative of a property associated with an intervertebral joint.

According to another mode of this aspect, the system provides useful information that is indicative of a property associated with an intervertebral disc.

According to another mode, the system provides useful information indicative of a degree of degradation of an intervertebral disc.

According to another mode, the system provides useful information indicative of a location where pain is being experienced in a patient.

According to another mode, the system provides the useful information based at least in part upon an NMR spectrum of the region of tissue.

Another aspect described hereunder is a medical diagnostic system configured to provide useful information that is indicative of a property of a first region of tissue based upon a magnetic resonance (NMR) spectrum of the first region, and wherein the property is associated with at least one of tissue degeneration and pain.

Another aspect described hereunder is a medical diagnostic system configured to provide useful information that is indicative of a property of a first region of tissue based upon a nuclear magnetic resonance (NMR) spectrum of the first region, and wherein the property is associated with tissue degeneration.

Another aspect described hereunder is a medical diagnostic system configured to provide useful information that is indicative of a property of a first region of tissue based upon a nuclear magnetic resonance (NMR) spectrum of the first region, and wherein the property is associated with pain.

Another aspect described hereunder is a system for identifying or characterizing a property of a first region of tissue associated with a skeletal joint. This aspect includes a processor that is configured to process data related to an NMR spectrum of the tissue in a manner that provides useful information that is indicative of the property in the first region of tissue.

Another aspect described hereunder is a system for identifying or characterizing a property of a first region of tissue associated with a skeletal joint. This particular aspect includes an NMR spectroscopy system that is configured to provide an NMR spectrum of the first region of tissue and to provide data related to the spectrum in a form that is processable to provide useful information that is indicative of the property in the first region of tissue.

Another aspect described hereunder is a system for identifying or characterizing a property of a first region of tissue associated with a skeletal joint. This aspect includes a substantially non-invasive imaging modality that is configured to provide imaging data related to the first region of tissue in a form that is processable to provide useful information that is indicative of the property in the first region of tissue.

Another aspect described hereunder is a system for identifying a property of at least a first region of an intervertebral disc. This aspect includes an NMR spectroscopy system adapted to provide data related to an NMR spectrum of the first region of tissue in a form that is processable to provide useful information that is indicative of the property in the first region of tissue.

Another aspect described hereunder is a system that provides useful information for diagnosing a property of a first region of tissue that is associated with tissue degeneration or pain. This aspect includes a computer readable software program in computer readable media form and that is configured to process data from a nuclear magnetic resonance (NMR) spectrum taken from the first region of tissue. The program is further configured to provide the useful information from the processed data.

Another aspect of the invention is a system for identifying, characterizing, and/or localizing a property of tissue associated with a skeletal joint. Such aspect may further include any one or more of the various aspects, modes, embodiments, variations, or features herein shown or described, or combinations thereof.

According to one mode of this aspect, the system is adapted to provide information indicative of a degree of a property of at least a portion of an intervertebral disc.

Another aspect is a system for identifying or characterizing a property of tissue associated with a skeletal joint in a patient. This includes at least one of: a processor that is configured to process information related to NMR spectroscopy of the tissue in a manner that is adapted to allow a degree of the property to be identified or characterized; an NMR spectroscopy systems that is configured to provide spectroscopic information related to the tissue such that a degree of the property may be identified or characterized; or a substantially non-invasive imaging modality that is configured to provide information regarding the tissue such that a degree of the property may be identified or characterized. Or, the system may include a combination of two or more of the foregoing.

According to one mode of this aspect, the information is related to a degree of a property of at least a portion of an intervertebral disc.

Another aspect of the invention is a system for characterizing at least a portion of an intervertebral disc with respect to a degree of a property of that disc. This system includes an NMR spectroscopy system adapted to capture a spectrum related to the portion. The spectrum provides information that is useful to indicates at least in part the degree of the property.

According to one further embodiment of the foregoing aspects and modes, the respective system is adapted to produce the information based on either or both of an annular portion or a nucleus portion of the intervertebral disc.

According to another embodiment, the system is adapted to display a curve related to the spectrum, and a portion of the curve provides the information.

According to another embodiment, the information is adapted to distinguish a degree of degradation of the disc. According to one highly beneficial further embodiment, the information is adapted to distinguish as to the degree of degradation by reference to a Thompson scale.

According to another embodiment, the property comprises at least one of pain, or at least one factor that correlates with pain.

According to another embodiment, the information is related to ratios of the resonances in the N-acetyl to choline regions, and choline to carbohydrate regions of the spectra.

According to another embodiment, the information is related to chondroitan sulfate, or a metabolite or degradation product thereof.

According to another embodiment, the information relates to at least one of $T_1$ and $T_2$ relaxation times of chemical constituents of disc spectra.

According to another embodiment, the property comprises at least one of a degree of dehydration of the disc, a degree of breakdown of a proteoglycan matrix of the disc, and a degree in a breakdown of a collagen matrix.

According to another embodiment, the system further includes a proton high resolution magic angle spinning spectroscopy system that is adapted to produce the information.

Another aspect of the invention is a method for identifying or characterizing a property of tissue associated with a skeletal joint. One or more of the foregoing method aspects, modes, embodiments, variations, or features herein described, or combinations thereof, may be employed to advance this method.

One further mode of this aspect further includes providing information indicative of a degree of a property of at least a portion of an intervertebral disc.

Another aspect is a method for identifying or characterizing a property of tissue associated with a skeletal joint in a patient, and includes at least one of the following steps: processing information related to NMR spectroscopy of the tissue in a manner that is adapted to allow a degree of the property to be identified or characterized; providing spectroscopy information from an NMR spectroscopy system and that is related to the tissue such that a degree of the property may be identified or characterized; or providing information regarding the tissue from a substantially non-invasive imaging modality with respect to the tissue and such that a degree of the property may be identified or characterized. Or a combination of one or more of the foregoing may be used.

One mode of this aspect includes determining a degree of a property of at least a portion of an intervertebral disc based upon the information.

Another aspect of the invention is a method for characterizing at least a portion of an intervertebral disc with respect to a degree of a property thereof, and includes capturing a spectrum related to the portion using an NMR spectroscopy system. The spectrum provides information that indicates at least in part the degree of the property.

According to one embodiment of the various method aspects and modes just described, the information produced is based on either or both of an annular portion or a nucleus portion of the intervertebral disc.

In another embodiment, a curve is displayed that is related to the spectrum, and wherein a portion of the curve provides the information.

Another embodiment includes distinguishing a degree of degradation of the disc based upon the information. A still further embodiment includes distinguishing the degree of degradation of the disc in relation to a Thompson grade based upon the information.

Another embodiment includes correlating the disc with degree of pain, or at least one factor that correlates with pain, based upon the information.

According to another embodiment, the information is related to a ratio of at least one of the resonances in the N-acetyl to choline regions, and choline to carbohydrate regions, of the spectra.

According to another embodiment, the information is related to chondroitin sulfate, or a metabolite or degradation product thereof.

According to another embodiment, the information relates to at least one of $T_1$ and $T_2$ relaxation times of chemical constituents of disc spectra.

According to another embodiment, the property relates to at least one of a degree of dehydration of the disc, a degree of breakdown of a proteoglycan matrix of the disc, and a degree in a breakdown of a collagen matrix.

Another embodiment includes producing the information at least in part using a proton high resolution magic angle spinning spectroscopy system.

Further to various of the aspects described hereunder, additional modes include beneficial non-invasive analysis of tissue properties based upon at least one of lactate-related, proteoglycan-related, or collagen-related chemical signatures recognized within the tissue. Particular beneficial modes include, for example, comparing ratios of recognized features of these signatures, and in one highly beneficial embodiment are based upon NMR resonances of such factors. Of further benefit as provided in the present embodiments, comparisons of two or more such resonances, such as for example in particular their peaks or other features indicating the extent of their presence, are made to provide distinguishing results that indicate a degree of a particular condition in the subject tissue (such as for example extent of degeneration or pain).

One additional particularly beneficial mode of the aspects provided hereunder includes use of NMR spectroscopy. In one embodiment, such spectroscopy involves equipment operating at above 8 Tesla, and in further embodiment at between about 11 and 12 Tesla. In another embodiment, the equipment operates at between about 4 and 10 Tesla, such as in particular at about 7 Tesla. In another embodiment, it operates at between about 2 and 4 Tesla, such as at about 3 Tesla. In another embodiment, it operates at below 3 Tesla, such as for example at about 1.5 Tesla. In this regard, 3T MRI systems are considered to provide substantial benefit for spectroscopic imaging & diagnosis of tissue regions within human patients, such as skeletal joints and in particular spinal joints and intervertebral discs. For lower Tesla equipment, still further embodiments contemplate using pass filter augmentation, amplification, or gain of signals falling within particular ranges targeted, such as certain particular peak resonant frequencies targeted as recognized signatures correlating with certain factors to be examined for the intended non-invasive diagnosis.

In additional embodiments, local coils may be used in MRI systems for enhanced magnetic resonance data acquisition. For example, local coils similar to those previously disclosed and developed for head and neck imaging may be used around skeletal joints for purposes of acquiring data useful according to the present aspects of this disclosure. In one particular embodiment, a local spine coil is used.

Particular beneficial embodiments of the present aspects include useful analysis of ratios between regions of NMR spectra that represent different chemical constituents in tissue regions being evaluated. It is appreciated that while using such ratios, and in particular certain specific ratios herein described, the individual components of such ratios representing individual spectral regions associated any one of a number of chemical constituents, and in particular those herein described with some specificity, are also considered useful data under the broad aspects and modes and thus represent further embodiments contemplated hereunder.

Another aspect of the present disclosure evaluates N-Acetyl/cho NMR spectral peak ratios tissue, with decreased values providing a measure of tissue degeneration useful in patient diagnosis. In a further mode, extent of localized pain is diagnosed based upon such evaluation. In another further mode the tissue evaluated is intervertebral disc tissue, and according to one embodiment includes at least a portion of a nucleus pulposus.

Another aspect of the present disclosure evaluates N-Acetyl/cho NMR spectral peak ratios in tissue, with increased values providing a measure of degeneration useful in patient diagnosis. In a further mode, extent of localized pain is diagnosed based upon such evaluation. In another further mode the tissue evaluated is intervertebral disc tissue, and according to one embodiment includes at least a portion of a nucleus pulposus.

Another aspect of the present disclosure evaluates choline-related NMR spectral peaks in tissue, with increased values providing a measure of disc degeneration useful in patient diagnosis. In a further mode, extent of localized pain is diagnosed based upon such evaluation. In another further mode the tissue evaluated is intervertebral disc tissue, and according to one embodiment includes at least a portion of a nucleus pulposus.

Another aspect evaluates one or more NMR spectral peak ratios in a target tissue region, compares those values against similar NMR spectral peak ratios in other adjacent or reference tissue, and determines extent and localization of tissue degeneration and/or pain based upon such comparison.

Each aspect, mode, embodiment, variation, or feature herein described is considered independently beneficial without requiring combination with the others. However, such further combinations and sub-combinations thereof are also considered yet further beneficial independent aspects invention.

Further aspects of the invention will be brought out in the following portions of the specification, including without limitation as presented in the claims, and wherein the detailed description is for the purpose of describing exemplary and preferred embodiments of the invention without necessarily placing limitations thereon, though such preferred embodiments may be described as providing particularly valuable benefits and uses.

BRIEF DESCRIPTION OF THE SEVERAL VIEWS OF THE DRAWING(S)

The invention will be more fully understood by reference to the following drawings which are for illustrative purposes only:

FIGS. 1X, 1Y, 1Z show a representative 1-D HR-MAS spectra acquired a Thompson Grade 1 disc (FIG. 1X) from the annulus fibrosus region (spectra at FIG. 1Y) and the nucleus pulposus region (spectra located at FIG. 1Z).

FIGS. 2X, 2Y, 2Z show representative 1-D HR-MAS spectra acquired for a Thompson Grade 3 disc (FIG. 2X) from the annulus fibrosus region (FIG. 2Y) and the nucleus pulposus region (FIG. 2Z). Resolvable peaks include: A:isoleucine, leucine, valine; B:lactate, isoleucine; C:alanine; D:isoleucine, leucine; E:lysine, leucine; F:N-Acetyl resonance of chonroitin sulfate; G:glutamine; H:glutamate, proline; I:glutamine, hydroxyproline; J:lysine; K:choline; L:phosphocholine; M:hydroxyproline; N:glycine; O:C—H resonances of chondroitin sulfate; P:ethanoloamine; the bracketed region indicates the C—H resonances of chondroitin sulfate.

FIGS. 3X, 3Y, 3Z show representative 1-D HR-MAS spectra acquired for a Thompson Grade 5 disc (FIG. 3X) from the annulus fibrosus region (FIG. 3Y) and the nucleus pulposus region (FIG. 3Z). Resolvable peaks include: A:isoleucine, leucine, valine; B:lactate, isoleucine; C:alanine; D:isoleucine, leucine; E:lysine, leucine; F:N-Acetyl resonance of chonroitin sulfate, Proline, glutamate; G:glutamine; H:glutamate, proline; I:glutamine, hydroxyproline; J:lysine; K:choline; L:phosphocholine; M:hydroxyproline; N:glycine; O:C—H resonances of chondroitin sulfate; P:ethanoloamine.

FIGS. 4A-4D show, as described in Table 1, the graphical representation of the distribution of integrated N-Acetyl/Cho (FIG. 4A) and Cho/Carb (FIG. 4B) of the annulus fibrosus as well as N-Acetyl/Cho (FIG. 4C) and Cho/Carb (FIG. 4D) of the nucleus pulposus with respect to Thompson Grade. Cho/Carb shows the largest statistical significance.

FIG. 5A shows a rotor synchronized adiabatic TOCSY spectrum of healthy disc material, with an 80 ms mixing time. The horizontal axis is the sum of projections and the vertical axis is a high-resolution 1-D spectrum. The three-letter amino acid code was used to designate amino acid crosspeaks.

FIGS. 8A and 8B show a T2-weighted MRI image of an ex-vivo bovine spine specimen, and corresponding NMR spectrum of a voxel region in a disc nucleus of the spine, respectively, according to certain present embodiments.

FIGS. 9A and 9B show similar respective images for the ex-vivo bovine spine featured in FIGS. 8A-B, taken at a first time interval after Papain injection into the disc evaluated.

FIGS. 10A and 10B show similar respective images for the ex-vivo bovine spine featured in FIGS. 8A-B, taken at a second time interval after Papain injection into the disc evaluated.

FIGS. 11A and 11B show similar respective images for the ex-vivo bovine spine featured in FIGS. 8A-B, taken at a third time interval after Papain injection into the disc evaluated.

FIGS. 12A and 12B show a T2-weighted MRI image of another ex-vivo bovine spine specimen, and corresponding NMR spectrum of a voxel region in a disc nucleus of the spine, respectively, according to certain present embodiments.

FIGS. 13A and 13B show similar respective images for the ex-vivo bovine spine featured in FIGS. 12A-B, taken at a first time interval after Papain injection into the disc evaluated.

FIGS. 14A and 14B show similar respective images for the ex-vivo bovine spine featured in FIGS. 12A-B, taken at a second time interval after Papain injection into the disc evaluated.

FIGS. 15A and 15B show similar respective images for the ex-vivo bovine spine featured in FIGS. 12A-B, taken at a third time interval after Papain injection into the disc evaluated.

FIGS. 16A and 16B show a T2-weighted MRI image of a cadaveric spine specimen, and corresponding NMR spectrum of a voxel region in a disc nucleus of the spine, respectively, according to certain present embodiments.

FIGS. 17A and 17B show a T2-weighted MRI image of another cadaveric spine specimen, and corresponding NMR spectrum of a voxel region in a disc nucleus of the spine, respectively, according to certain present embodiments.

FIGS. 18A and 18B show a T2-weighted MRI image of another cadaveric spine specimen, and corresponding NMR spectrum of a voxel region in a disc nucleus of the spine, respectively, according to certain present embodiments.

FIGS. 19A and 19B show a T2-weighted MRI image of another cadaveric spine specimen, and corresponding NMR spectrum of a voxel region in a disc nucleus of the spine, respectively, according to certain present embodiments.

FIGS. 20A and 20B show a T2-weighted MRI image of another cadaveric spine specimen, and corresponding NMR spectrum of a voxel region in a disc nucleus of the spine, respectively, according to certain present embodiments.

DETAILED DESCRIPTION OF THE INVENTION

Figure 5A:
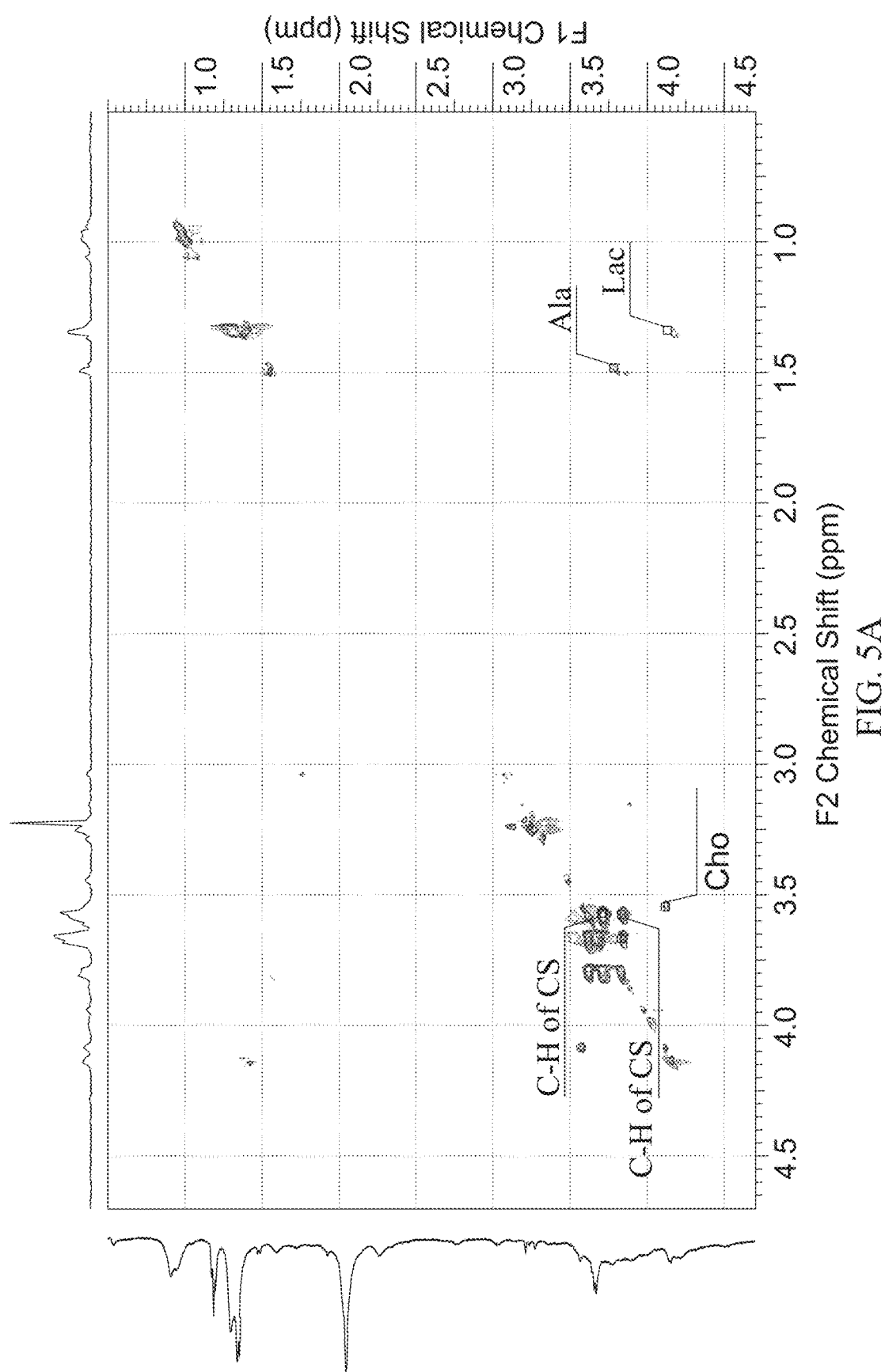
FIG. 5B shows a rotor synchronized adiabatic TOCSY spectrum of degenerate disc, with an 80 ms mixing time. In the degenerate spectrum there is an increase in signal in the amino acids as well as choline containing compounds, which are not present in the healthy spectrum.
Figure 5B:
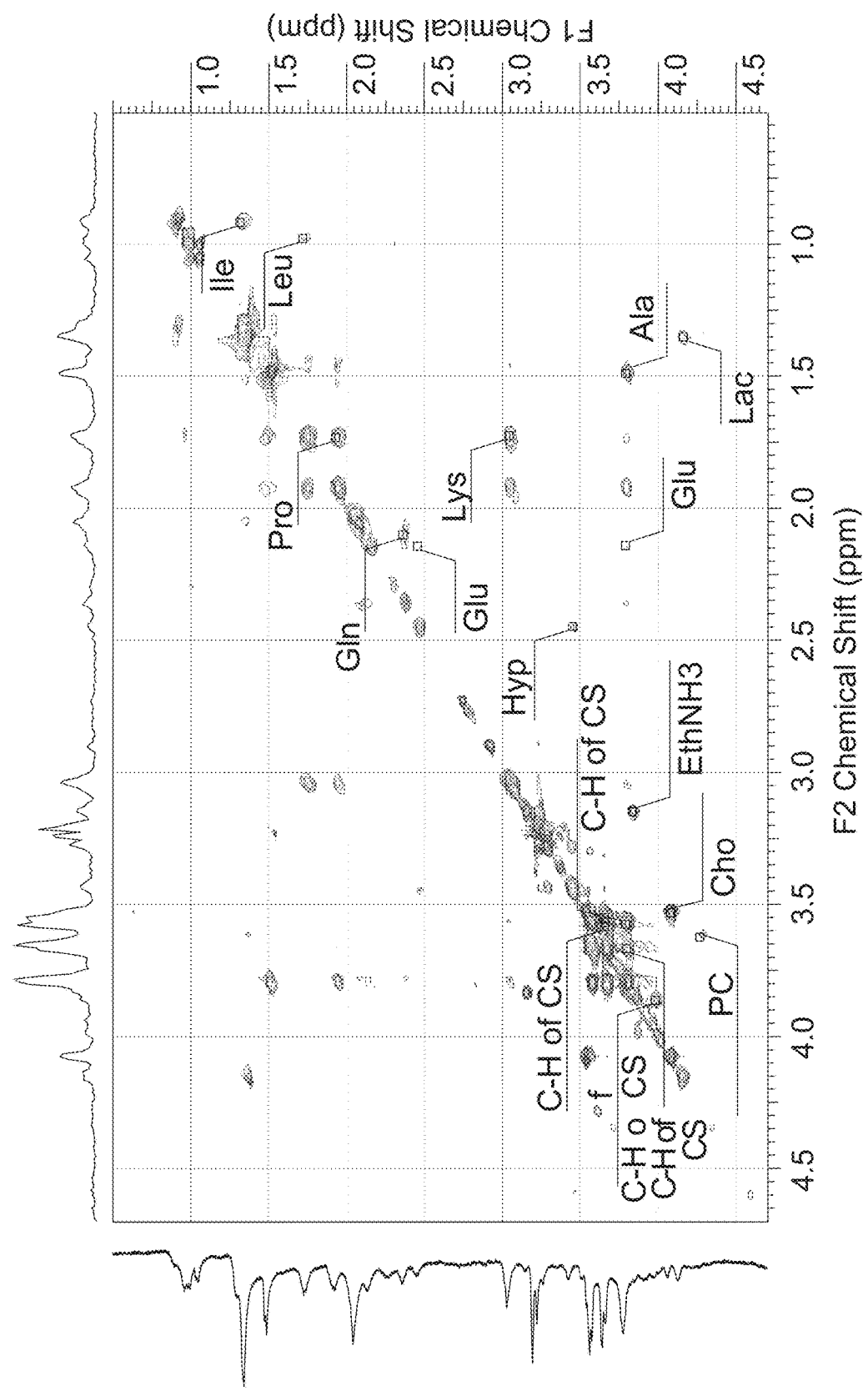
Figure 6A:
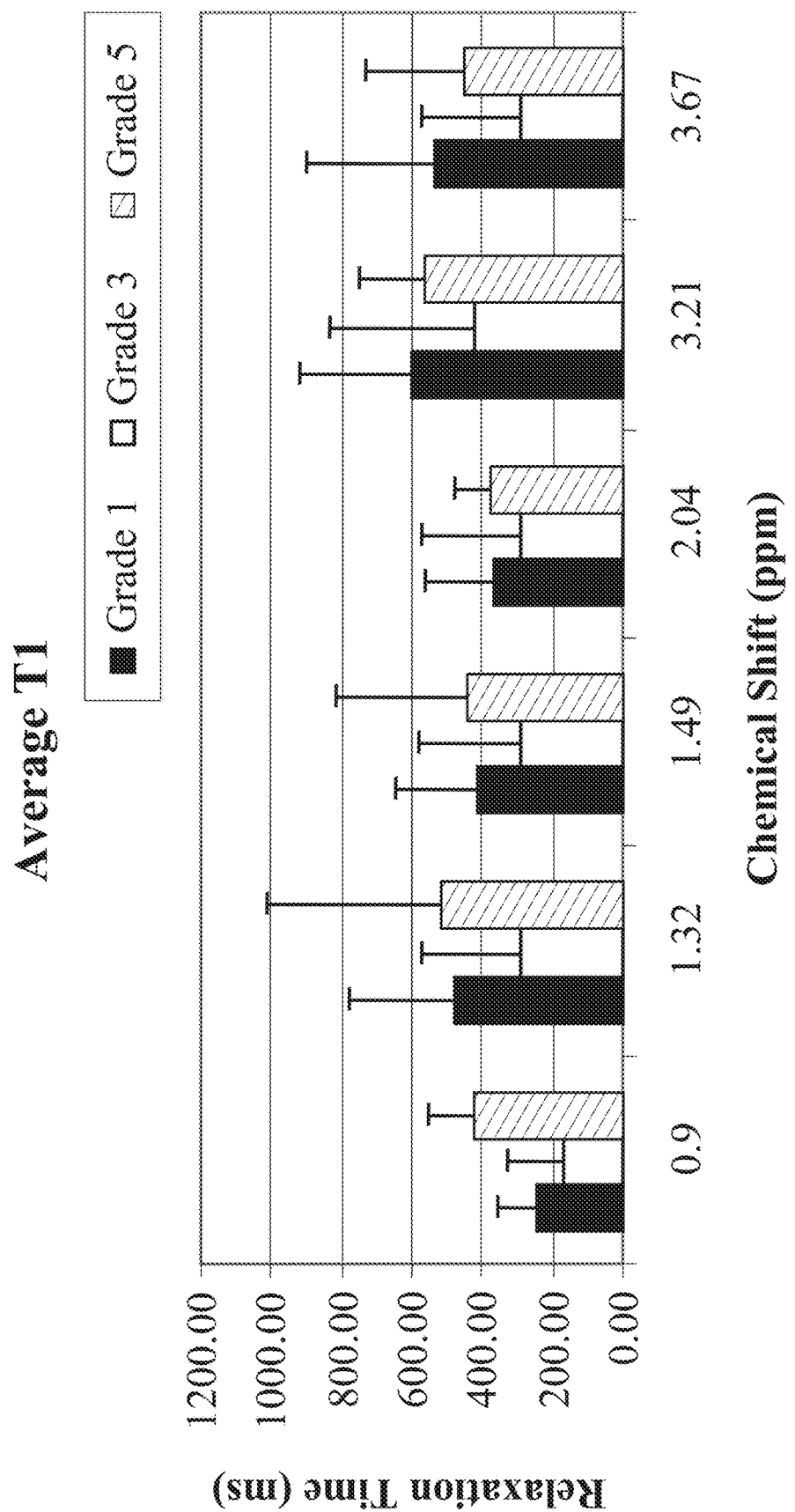
FIG. 6A shows a graphical representation of the average spin-lattice relaxation times of the following compounds: 0.9 ppm: Isoleucine, Leucine, and Valine, 1.32 ppm: Lactate, 1.49 ppm: Alanine, 2.04 ppm: N-Acetyl moiety of Chondroitin sulfate, 3.21 ppm: Choline containing compounds, 3.67 ppm: C—H of the carbohydrate residue associated with the Chondroitin sulfate polymer.
Figure 6B:
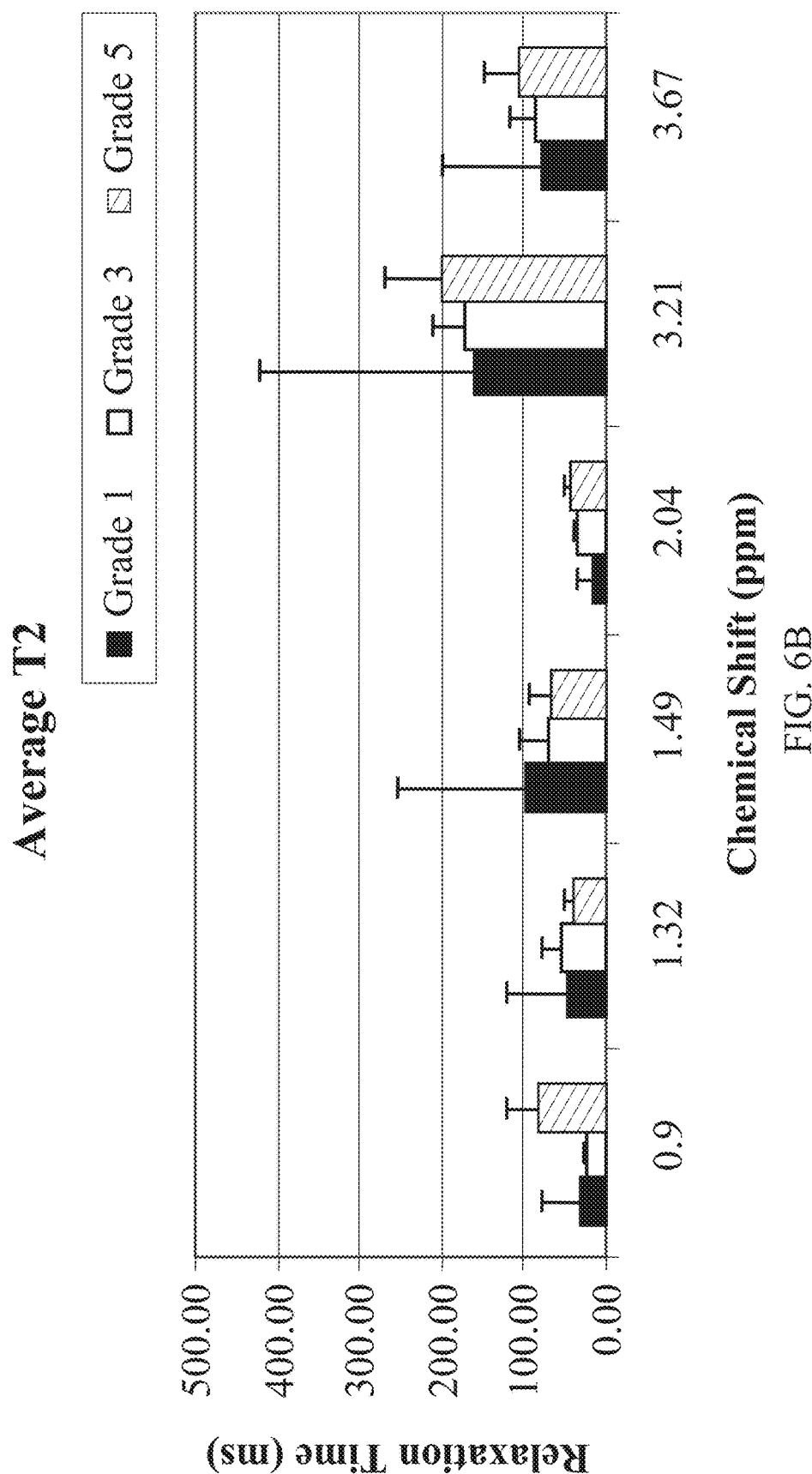
FIG. 6B shows a graphical representation of the average spin-spin relaxation times of the previously mentioned compounds. (*) Denotes peaks with very large standard deviations due to low signal intensity.
Figures 7A, 7B:
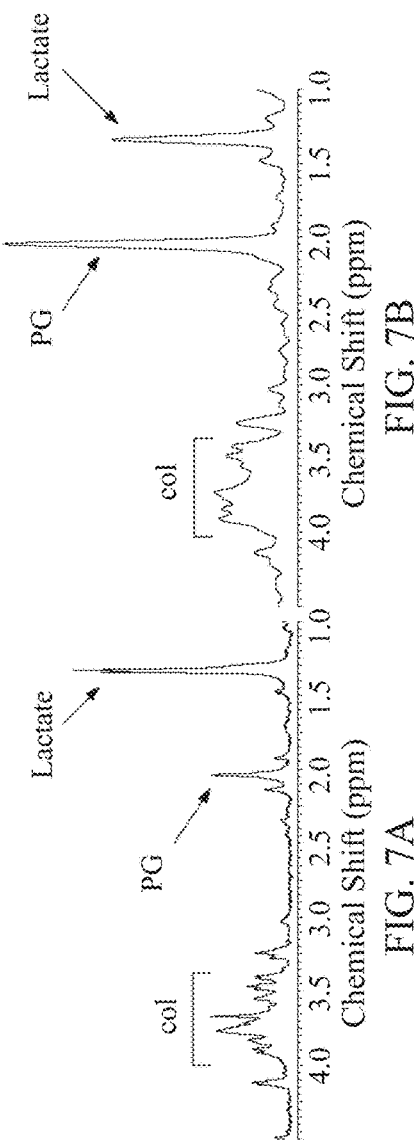
FIGS. 7A, 7B show exemplary spectra taken from an experiment performed on certain intervertebral discs using NMR spectroscopy.

Referring more specifically to the drawings, for illustrative purposes the present invention is embodied in the apparatus generally shown in FIG. 1X through FIG. 6B and Table 1, and as further developed according to certain particular modes as reflected in FIGS. 7A-B and Table 2. It will be appreciated that the apparatus may vary as to configuration and as to details of the parts, and that the method may vary as to the specific steps and sequence, without departing from the basic concepts as disclosed herein.

The ability to characterize disc degeneration in regard to particular material or chemical constituents using NMR spectroscopy is herein disclosed. Non-invasive correlations between NMR spectra indicia and Thompson grade are made, yielding tremendous benefit to various uses in medicine and research. The present invention is highly beneficial with respect to providing a non-invasive ability to identify and characterize markers associated with the particular state or locality of disc degeneration, and in further particular relation to localization of pain or pain generating factors.

Various aspects, modes, embodiments, variations, and features of the present invention will be made clear by reference to one or more experimental studies performed, and accompanying discussion, as provided by way of one or more examples immediately below.

EXAMPLE 1

1. Overview

The goal of this study was to determine the ability of high-resolution magic angle spinning (HR-MAS) NMR spectroscopy to distinguish different stages of intervertebral disc degeneration. 17 discs were removed from human cadavers and analyzed using one- and two-dimensional (TOCSY) $^1$H HR-MAS spectroscopy, and $T_1$ and $T_2$ relaxation time measurements to determine the chemical composition and changes in chemical environment of discs with increasing levels of degeneration (Thompson grade). Significant findings include that spectra were very similar for samples taken from annular and nuclear regions of discs and that visually apparent changes were observed in the spectra of the annular and nuclear samples from discs with increasing Thompson grade. Area ratios of the N-Acetyl to choline regions, and choline to carbohydrate regions of the spectra allowed for discrimination between discs of increasing Thompson grade with minimal overlap of individual ratios. Changes in $T_1$ and $T_2$ relaxation times of the chemical constituents of disc spectra seemed to reflect both changes in dehydration of the disc and the degree of breakdown of the proteoglycan and collagen matrices with increasing Thompson grade. The results of this study support the using of in vivo spectroscopy for detecting chemical changes associated with disc degeneration.

Several in vivo MRI studies have been performed in an attempt to better characterize IVDD. $T_1$ and $T_2$ weighted MRI has been used to analyze the structure of intervertebral discs. A decrease in $T_2$-weighted signal intensity with increased lumbar disc degeneration has been alleged. $T_1$ values of water in degraded cartilage decrease significantly in samples with degeneration. Changes have been allegedly observed in $T_2$ relaxation times of water with degeneration of articular cartilage as well. Diffusion weighted imaging has also been used to study disc and cartilage, showing a decrease in water content as a correlate to a degenerative state. In MRI of the cervical spine, as age increases, dehydration occurs more evenly across all discs. One research group speculates that this is due to a more uniform degeneration than that due to injury or recurrent stress. These MR imaging findings increase the accuracy of a gross morphological grading system, but degenerative states could be more effectively and quantitatively measured using a method based on measurement of the chemical constituents detectable through in vivo spectroscopy.

There is currently a great need for non-invasive techniques to better characterize the metabolic composition of intact disc tissue in vivo. Conventional methods for determining chemical composition require the extraction of proteins through biochemical means, which in turn destroy the tissue and prevent further study (e.g., biological assays or mechanical tests). HR-MAS NMR spectroscopy is a nondestructive technique that has been successfully used to characterize the composition of various intact biological tissues. Cartilage degeneration has been modeled using collagenases which degrade bovine nasal cartilage, and the degradation products have been studied using high-resolution magic angle spinning (HR-MAS) NMR spectroscopy. This allowed the amino acid products of the collagen triple helix to be compared to the natural degradation of bovine tissue and provided a model of human tissue degradation. However, the differing levels of biochemical and mechanical degradation associated with varying degrees of intermediary degradation are still characterized using a single Thompson Grade, which underscores the need for a more descriptive grading scale than the current method.

The purpose of this study was to demonstrate use of HR-MAS spectroscopy to assess the chemical changes associated with intervertebral disc degeneration. Suitable modifications and adaptations of these HR-MAS tools and methods may thus be made in order to measure and correlate similar metabolic changes when performing in vivo magnetic resonance spectroscopy for characterizing degree of disc degeneration.

HR-MAS spectroscopy was applied to intervertebral discs spanning a range of Thompson grades in order to identify the NMR observable chemicals and to determine the difference in the ratios of these chemicals between discs at different stages of degeneration. Relaxation time measurements were also performed to characterize changes in the environment of chemical disc constituents with disc degeneration and their molecular degrees of freedom.

2. Materials and Methods

A. Tissue Acquisition

This study was approved by our Institutional Review Board. Lumbar spines were surgically removed from n=17 human cadavers (range: 22 to 85 years) and frozen at −80° C. The harvested spines were then separated with an autopsy saw and scalpel. The surrounding bone of the intervertebral body was removed and separated from the intervertebral disc. 3 mm biopsy punches were taken in the annulus fibrosus and nucleus pulposus regions of the removed discs. These punches were taken in close proximity to one another and were cylindrically symmetrical. The average mass was 15.2±3.4 mg. Three side-by-side samples, from a given location, were also used to test for spectral reproducibility. The Thompson Grading was performed in consensus readings with adherence to the Thompson Grading scale. Altogether, 8 Thompson grade 1, 6 Thompson grade 3 and 6 Thompson grade 5 samples were studied.

B. HR-MAS Data Acquisition

HR-MAS data were acquired at 1.0±0.5° C. and a 2,250 Hz spin rate using a Varian INOVA spectrometer operating at 11.75 T (500 MHz for $^1$H) and equipped with a 4 mm gHX nanoprobe. For one-dimensional spectra, 40,000 complex points were acquired over a 20,000 Hz (40 ppm) spectral width, with a 90° pulse width, 2s HOD presaturaturation period, 32 transients, 8 s repetition time (>5 times the longest $T_1$ relaxation time), 2 s acquisition time (>5 times the longest $T_2$ relaxation time), and a 3:36 min total acquisition time. Samples were analyzed using custom designed 18 µl zirconium rotors, containing an ellipsoid shaped sample chamber and an airtight screw top plug to prevent leakage. For each sample, 3.0 µl of deuterium oxide containing 0.75 wt % 3-(trimethylsilyl)propionic-2,2,3,3-$d_4$ acid ($D_2O$+TSP, Sigma-Aldrich) were pipetted into the bottom of the rotor, after which the tissue samples were weighed and then added.

Longitudinal ($T_1$) relaxation time measurements were acquired using an inversion recovery pulse sequence with variable delay times from 0.01 to 2.00 s. Transverse ($T_2$) relaxation time measurements were acquired using a rotor-synchronized (i.e., $\tau$ delay=n×(spin rate)$^{-1}$, where n is an even number) Carr-Purcell-Meiboom-Gill pulse sequence with echo times ranging from 10 to 128 ms. For two dimensional TOCSY spectra, 4096 complex points were acquired over a 20,000 Hz spectral width in the direct dimension ($F_2$), while 256 complex points were acquired over a 6,500 Hz spectral width in the indirect dimension ($F_1$). TOCSY spectra were acquired with a 2s HOD presaturation/relaxation delay, 0.2s acquisition time, 32 steady state pulses (1st increment only), 16 transients/increment, mixing times ranging from 10 to 80 ms, phase sensitive using States-Habercorn, for a total experiment time of approximately 5 hrs, 12 min. To minimize the effects of $B_0$ and $B_1$ inhomogeneities, rotor-synchronized constant adiabaticity WURST-8 adiabatic pulses (33) were used for isotropic mixing, and were generated using the "Pandora's Box" pulse shape generator (Pbox, Varian) with a $B_1$ field of 6,500 Hz and duration of 444 ms (1/spin rate). One-dimensional spectra were acquired before and after each two-dimensional experiment to assess metabolic degradation. $T_1$ and $T_2$ relaxation time measurements were taken from the nucleus (n=9) and the annulus (n=12) of healthy and degenerate discs.

C. Data Processing

Data were processed online using Varian VNMR 6.1C software (Varian, Inc., Palo Alto), or offline using ACD/Labs 1D and 2D NMR processing software, version 7.0 (Advanced Chemistry Development, Inc. Toronto). One dimensional FIDs were apodized with an exponential function, with a line broadening factor equal to the inverse of the acquisition time, Fourier transformed, phase corrected, and referenced to TSP at 0.0 ppm. Relaxation times were calculated using exponential least squares regression analysis. Relaxation times were only used if the list (least) squares fit had a standard error of less than 10%. TOCSY data were processed using 3×N linear predictions in $F_1$, zero filled to 1024 complex points ($F_1$ only), and apodized using Gaussian weighting in both dimensions.

Cross peaks were assigned using previously reported chemical shift values from the literature. Based upon visual assessment of the data, three spectral regions from the 1D data were binned as follows: the N-acetyl region (1.90-2.10 ppm); the choline head group (Cho) region (3.15-3.30 ppm); and the carbohydrate (Carb) region (3.50-4.20 ppm). Three ratios, abbreviated N-Acetyl/Cho, Cho/Carb, and N-Acetyl/Carb, were then calculated for each spectrum, after setting the integrated area of the carbohydrate region to 1.00. For each Thompson grade, the mean ratios and standard deviations were calculated and a Student's t test was performed to determine the statistical significance of the data, where a p-value <0.05 was considered significant.

3. Results

A. Thompson Grade Differentiation

Representative one-dimensional HR-MAS spectra of the annular and nuclear regions of intervertebral discs with Thompson grades 1, 3, and 5 are shown in FIGS. 1-3.

Figures 1X, 1Y, 1Z:
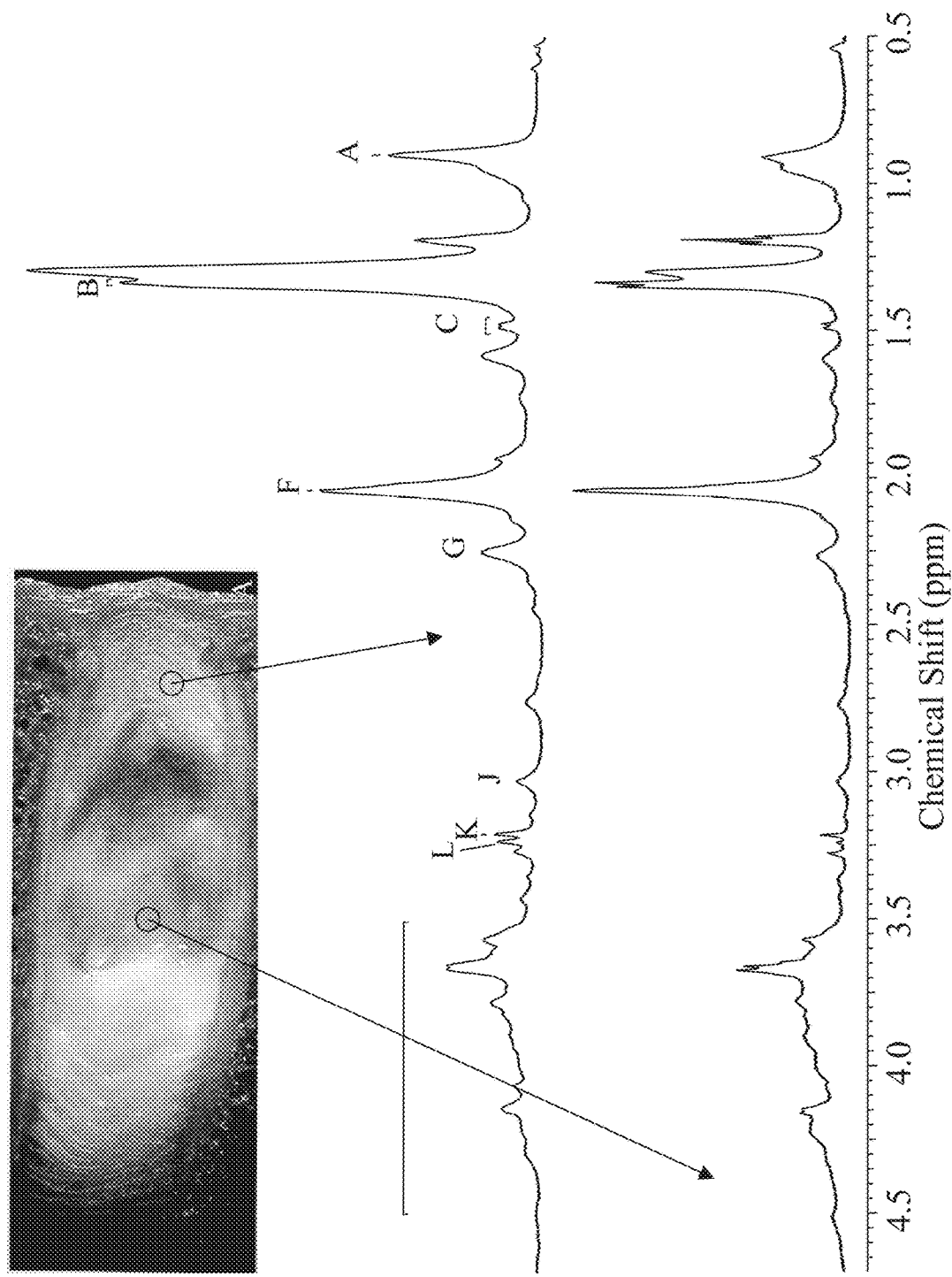

FIGS. 1X, 1Y, 1Z show a representative 1-D HR-MAS spectra acquired from a Thompson Grade 1 disc (FIG. 1X) from the annulus fibrosus region (spectra at FIG. 1Y) and the nucleus pulposus region (spectra located at FIG. 1Z). Arrows illustrate associations between the various spectra shown at FIGS. 1Y, 1Z and the respective representative portion(s) of the disc being evaluated and shown at FIG. 1X. The circles indicate the representative location of 3 mm punch biopsies taken from the disc. Resolvable peaks include: A:isoleucine, leucine, valine; B:lactate, isoleucine; C:alanine; F:N-Acetyl resonance of chonroitin sulfate; G:glutamine; J:lysine; K:choline; L:phosphocholine; the bracketed region indicates the C—H resonances of chondroitin sulfate.

Thompson grade 1 disc material is characterized by its stiff pliable annular ring and hydrated gel core (FIG. 1X). 3 mm punch biopsies were taken from annular and nuclear regions of intervertebral discs and the corresponding HR-MAS spectra are shown (FIG. 1Y, 1Z, respectively). Both HR-MAS spectra demonstrate a large N-acetyl resonance centered at 2.04 ppm, and carbohydrate resonances attributed to chondroitin sulfate in the region from 3.5 to 4.0 ppm. Additionally, resonances due to lactate (1.33 ppm), lipid (ppm), the choline head group (3.21-3.25 ppm), and several amino acids (alanine (1.49 ppm), isoleucine, leucine, and valine) are also observable. Interestingly, in lower Thompson grade discs, consistently greater spectral resolution was observed in the nucleus (FIG. 1Z) as compared to the annulus (FIG. 1Y).

Figures 2X, 2Y, 2Z:
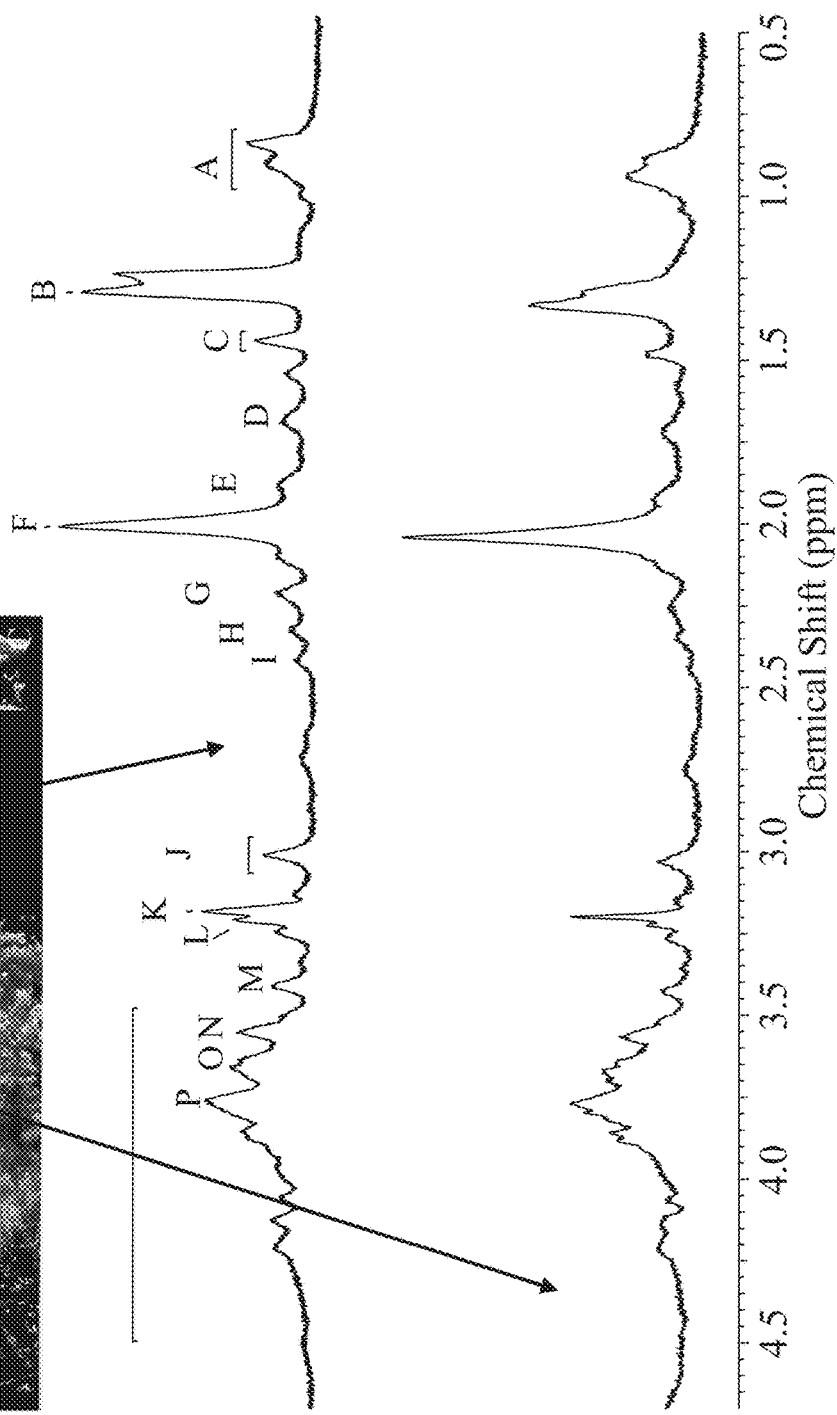
Figures 3X, 3Y, 3Z:
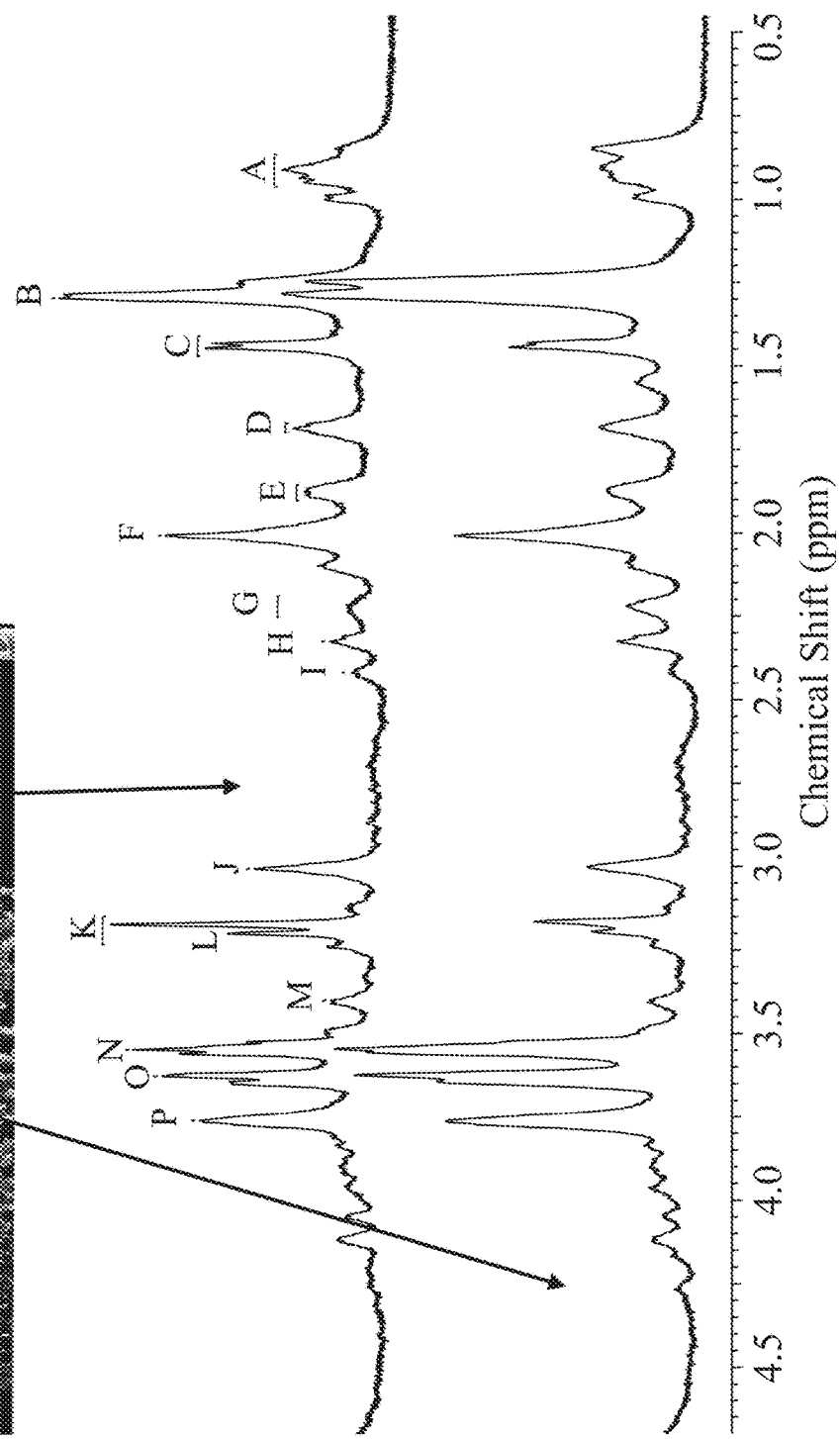
Figure 4A:
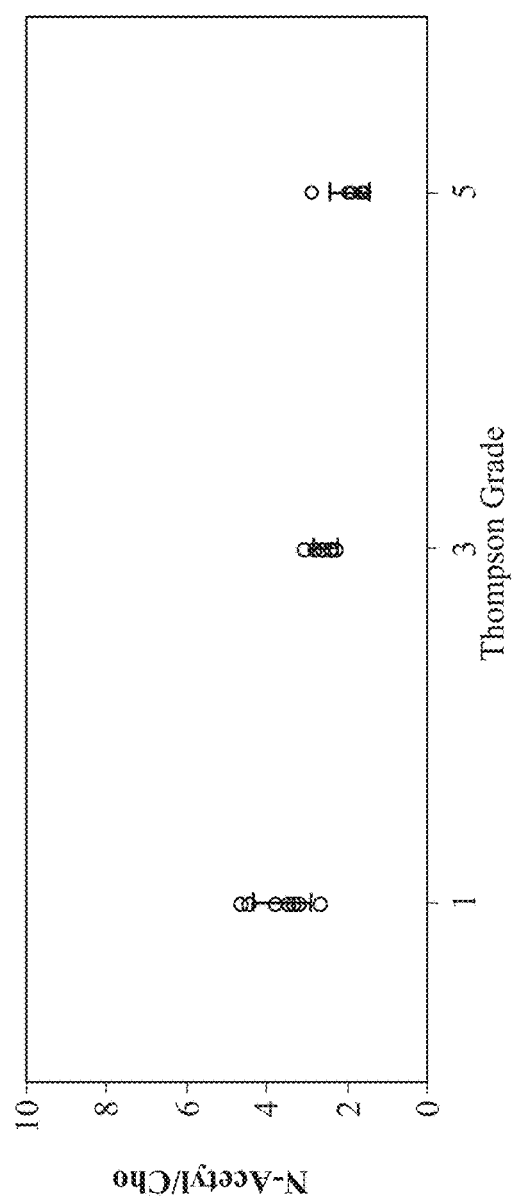
Figure 4B:
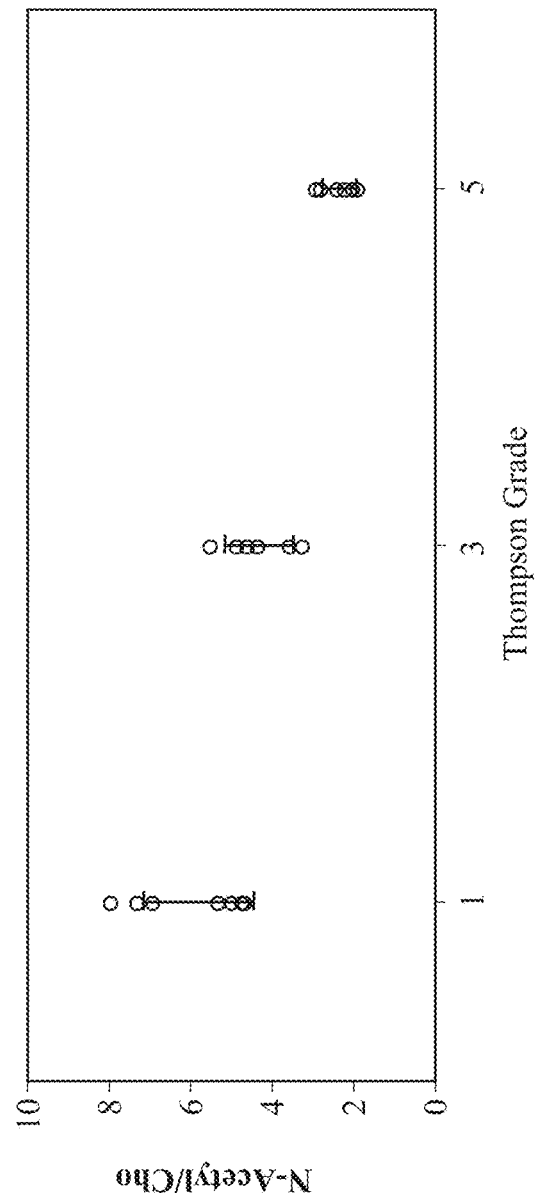
Figure 4C:
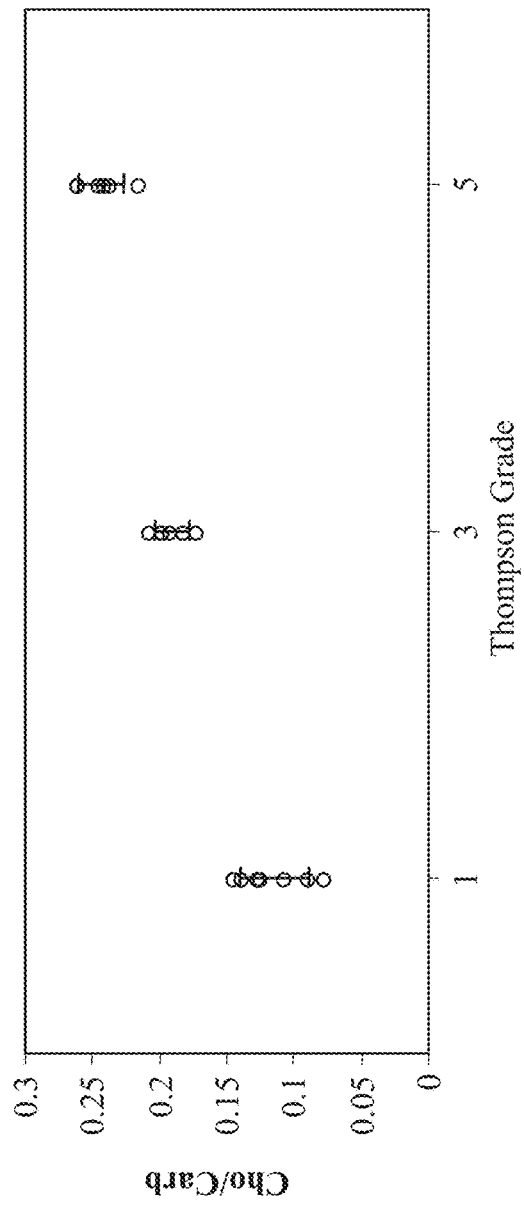
Figure 4D:
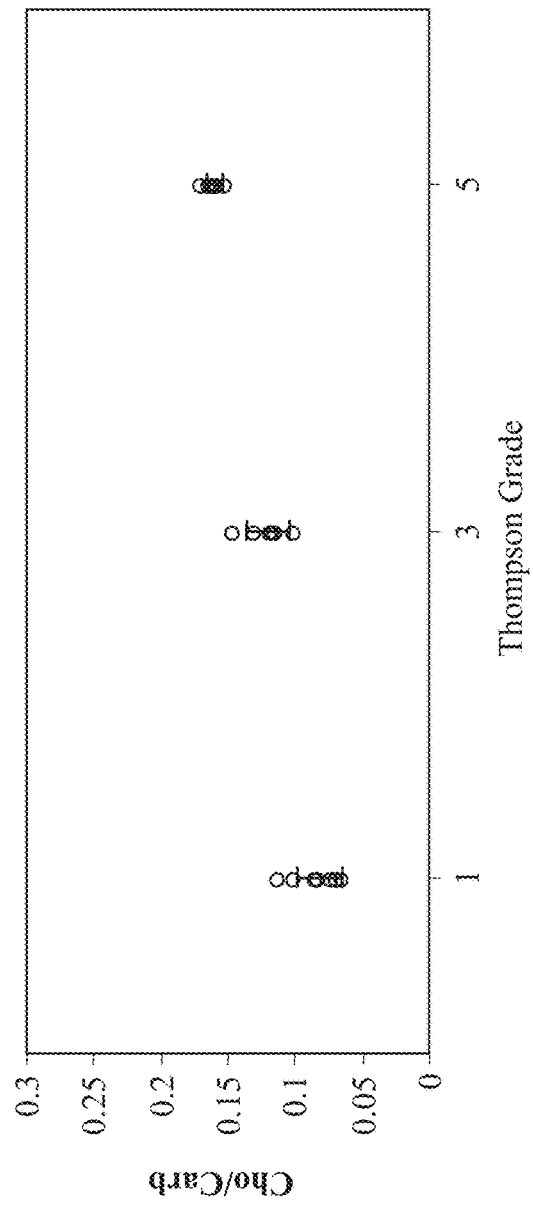

FIGS. 2X, 2Y, 2Z show a moderately degenerated Thompson Grade 3 disc (FIG. 2X) and corresponding HR-MAS spectra taken from the annulus fibrosus (FIG. 2Y) and the nucleus pulposus (FIG. 2Z). Morphological changes associated with Thompson grade 3 are dehydration of the disc coupled with a mechanical disruption of the disc matrix. Spectroscopically, the nucleus and annulus of Thompson Grade 3 demonstrate an increase in spectral resolution in the carbohydrate region of the spectrum compared to Thompson Grade 1 disc (FIG. 1X, 1Y, respectively). There is also an increase in the resonances containing the choline headgroup (3.21 ppm).

Thompson grade 5 discs (FIG. 3X) pathologically demonstrate a further dehydration of the disc, mucinous infiltration and extensive disruptions in the annulus, fibrous tissue replacement of the nucleus pulposus, and a loss of visual distinction between the annular and nuclear regions. Spectroscopically, there is a further increase in the resolution and intensity of the resonances in the choline and carbohydrate regions of the spectra. There is also a visual decrease in the intensity of the N-acetyl resonance and an increase in the number and intensity of resonances due to free amino acids.

Table 1 shows integral ratios for annulus fibrosus (A) and nucleus pulposus (B) and student's t-test results. Individual and mean±sdev N-Acetyl/Cho, Cho/Carb, and N-Acetyl/Carb ratios for Thompson grades 1, 3, and 5 discs are statistically compared. Thompson grades 2 and 4 discs were omitted from this study due to the subjectivity of the Thompson grading scale. For both the nucleus and annulus, the mean N-Acetyl/Cho, and Cho/Carb ratios showed significant differences between all three Thompson grades, while the N-Acetyl/Carb ratio was only significantly different between nucleus samples taken from Thompson 3 versus 5 discs.

For grades 1 vs. 3 the difference of ratios 1 and 2 were significant when comparing any two grades, for both the annulus and nucleus. N-Acetyl/Carb was only significant when comparing grade 1 to grade 5 of the nucleus. N-Acetyl/Cho=Integral (1.90-2.10 ppm)/Integral (3.15-3.30 ppm), Cho/Carb=Integral (3.15-3.30 ppm)/Integral (3.50-4.20 ppm), N-Acetyl/Carb=Integral (1.90-2.10 ppm)/Integral (3.50-4.20 ppm).

In FIGS. 4A-4D, individual N-Acetyl/Cho (FIGS. 4A and 4B), and Cho/Carb (FIGS. 4C and 4D) ratios from the annulus (top) and nucleus (bottom) for the three Thompson grades are plotted in order to assess the overlap of individual measurements. For the N-Acetyl/Cho ratio, there was no overlap of individual nucleus values between Thompson grade 1 and 5 discs, there was substantial overlap of individual values for all other comparisons. For the Cho/Carb ratio, there was no overlap of individual annulus values between all three Thompson grades and no overlap of individual nucleus values between Thompson grade 1 and 5.

B. Total Correlation Spectroscopy (TOCSY)

To assign the resonances observed in the one-dimensional proton spectra, two-dimensional TOCSY spectra were acquired and the chemical shifts of the crosspeaks observed were compared to previously reported chemical shift values. FIG. 5A shows a TOCSY spectrum of a Thompson grade 1 intervertebral disc. In all eight of the Thompson grade 1 discs studied, only a limited number of crosspeaks could be observed, including those due to alanine (1.49, 3.79 ppm), lactate (1.35, 4.16 ppm), and the protons related to the carbohydrate portion of the proteoglycan polymers. In contrast, the TOCSY spectrum of the six degenerated Thompson grade 5 discs studied (FIG. 5B), exhibited many more detectable crosspeaks, including isoleucine (0.92, 1.32 ppm), leucine (0.98, 1.72 ppm), lysine (1.73, 3.04 ppm), proline (1.73, 1.93 ppm), glutamine (2.14, 2.46 ppm and 2.14, 3.79 ppm), glutamate (2.1, 2.36 ppm), hydroxyproline (2.45, 3.45 ppm), and ethanolamine (3.15, 3.83 ppm). TOCSY experiments demonstrated that the resolvable resonances in the carbohydrate region (3.5-4.2 ppm) of the 1-D HR-MAS spectrum were composite peaks arising from multiple amino acids, ethanolamine containing compounds, as well as the sugar C—H protons of the breakdown products of chondroitin sulfate. The 1-D HR-MAS spectra of all discs studied exhibited two singlets at 3.21 and 3.23 ppm, which correspond to the chemical shifts of free choline (Cho) and phosphocholine (PC) respectively. TOCSY experiments also demonstrated cross peaks for the methylene protons of Cho at 3.55×4.07 ppm and PC at 3.62×4.18 ppm. There are also several other smaller, broader resonances in the choline region of the spectrum, which remain unidentified.

C. $T_1$ and $T_2$ Relaxation Times

FIGS. 6A and 6B, respectively, show the average $T_1$ and $T_2$ relaxation times for resolvable resonances in the Thompson Grade 1, 3, and 5 discs. Only $T_1$ and $T_2$ relaxation times of resonances that could be resolved in nucleus and annulus spectra of all of the Thompson grades were measured. This resulted in the measurement of $T_1$ and $T_2$ relaxation times for resonances at 0.9, 1.32, 1.49, 2.04, 3.21 and 3.67 ppm. There was no significant difference observed between $T_1$ and $T_2$ relaxation times measured in the nucleus and annulus, therefore the relaxation times of theses regions were combined to increase the statistical significance of the disc grade comparisons. The average $T_1$ and $T_2$ measurements for these resonances from each of the Thompson grades demonstrated large variability yielding no significant trend in metabolite $T_1$ and $T_2$ with increasing disc degeneration. However, there was an observable trend for $T_1$ relaxation times with increasing Thompson grade. The observable trend for $T_1$ values was an initial decrease for Thompson grade 3 discs and subsequent increase for Thompson grade 5 discs. For $T_2$, there was no consistent trend for all of the observed resonances, however, there was an increasing trend for the N-Acetyl (2.04 ppm), Choline (3.21 ppm) and the carbohydrate C—H resonances (3.67 ppm) with increasing Thompson grade.

4. Discussion

Proton HR-MAS spectra were very similar for samples taken from annular and nuclear regions of intervertebral discs, with both spectra demonstrating a large N-acetyl resonance and carbohydrate resonances primarily from chondroitin sulfate, as well as resonances from choline containing compounds, lipid/lactate and several amino acids. Due to the more gel like nature of the nucleus, consistently greater spectral resolution was observed in the nucleus as compared to the annulus for Thompson grade 1 discs.

A substantial result observed in this study was that significant, visually apparent changes were observed in the proton HR-MAS spectra of the annular and nuclear samples from discs with increasing Thompson grade. Specifically, there was a grade dependent increase in number of observable resonances and a sharpening of line widths of resonances in the 3.5-4.0 ppm region of the spectrum, corresponding to a loss of the "broad component" in this region. Additionally, there was an increase in the signal intensity of resonances in the choline containing compound region of the spectrum, and a relative decrease in the N-Acetyl resonance.

Similarly, the number and intensity of cross peaks in TOCSY disc spectra increased with increasing Thompson grade. A large number of the cross peaks appearing in TOCSY spectra of degraded nucleus and annulus were due to the amino acids hydroxyproline, proline, glycine, lysine, leucine, isoleucine, alanine, valine, glutamine and glutamate and ethanolamine, many of which are components of collagen. Amino acid resonances also dominate the 1-D proton HR-MAS spectra of both nucleus and annulus in Thompson grade 5 discs. The observation of amino acids due to the breakdown of collagen has been previously observed in NMR studies of cartilage digestion using metalloproteinases. Metalloproteinases (MMPs) have been suspected to play an important role in disc degeneration by disrupting the collagen matrix that supports the disc. As the collagen network disintegrates and the collagen helices break down into their constituent amino acids, those resonances become more visible in both 1D and 2D HR-MAS spectra.

There was also metabolic evidence of chondroitin sulfate breakdown with disc degeneration. This conclusion is based on the increase in intensity and resolution of carbohydrate C—H resonances (3.5-4.0 ppm) and the relative reduction in the N-Acetyl resonance of chondroitin sulfate (2.04 ppm) in proton HR-MAS spectra taken from the annulus and nucleus of Thompson grade 3 and 5 discs as compared to Thompson grade 1. Prior $^1$H and $^{13}$C HR-MAS NMR investigations on native and enzymatically digested bovine nasal cartilage have shown a change in the composition of the N-acetyl resonance from being initially the N-acetyl resonance in non-digested cartilage to a composite peak containing the N-acetyl and amino acid resonances. Chondroitin sulfate concentration decreases with disc degeneration. TOCSY studies have demonstrated that the resolvable resonances in the 3.5-4.0 ppm region of degenerated disc spectra also arise from a complex mixture of compounds including multiple amino acids, ethanolamine containing compounds and the C—H resonances of carbohydrates. The complete assignment of resonances in degenerated disk spectra will therefore require human disc digestion studies and correlation with biochemical assays for chondroitin sulfate (e.g. dimethylmethylene blue (DMMB) assay) and collagen (collagenase).

Based on the observed changes in the N-Acetyl resonance, and resonances in the choline and the carbohydrate/amino acid regions of the HR-MAS spectrum, the N-Acetyl/Cho, Cho/Carb, and N-Acetyl/Carb ratios were investigated to determine which ratios provided the best discrimination of Thompson grade. Both the mean N-Acetyl/Cho, and Cho/Carb ratios showed significant differences between all three Thompson grades, with the Cho/Carb ratio demonstrating the least overlap between individual values for all three Thompson grades.

The Cho/Carb ratio had no overlap between the three Thompson grades for spectra taken from the annulus and minimal overlap for spectra taken from the nucleus. This is in particular beneficial since, for in vivo spectroscopy, spectra acquisition solely from either the nucleus or annulus of the disc should thus not be required in many circumstances. This is a benefit due both to their close relative proximity and signal to noise considerations.

The N-Acetyl/Cho ratio may also prove useful for in vivo spectroscopy of disc degeneration since the N-Acetyl resonance is the largest peak in the Thompson 1 and 3 discs and it was reduced to level that was less than or equal to the choline and carbohydrate regions of the spectrum in Thompson grade 5 discs. In fact, Thompson grade 5 spectra from both the nucleus and annulus can be visually separated from Thompson grade 1 and 3 disc spectra based on the relative reduction of the N-acetyl peak to the choline and carbohydrate regions.

In prior studies, investigators have studied water spin-lattice and spin-spin relaxation times in an attempt to characterize disc and cartilage degeneration. More hydrated tissue is known to have a longer water $T_1$ and $T_2$ and are shortened with disc degeneration, presumably due to tissue water loss (14). No prior reports correlate $T_1$ and $T_2$ changes of the disc degenerative products with Thompson grade.

In this study the average $T_1$ and $T_2$ measurements of the disc breakdown products demonstrated large variability. However, there was an observable trend in $T_1$ relaxation times. The trend for $T_1$ values was an initial decrease for Thompson grade 3 discs and subsequent increase for Thompson grade 5 discs. The observed initial shortening of breakdown products $T_1$'s in Thompson grade 3 discs could be for example due to the loss of water with disc degeneration. The subsequent increase of $T_1$'s in Thompson grade 5 discs could be for example due to an increase in mobility of the breakdown products as they are released from the proteoglycan and collagen matrices.

Regarding observed changes in $T_2$, no clear trend exists across all the breakdown products. $T_1$ and $T_2$ measurements of both water and degradation products in larger numbers of degenerated discs would provide further useful information to understand the relaxation times measured in this study.

5. Summary

In summary, proton HR-MAS provides spectra that are very similar for samples taken from annular and nuclear regions of intervertebral discs. Significant, visually apparent changes are observable in the proton HR-MAS spectra of the annular and nuclear samples from discs with increasing Thompson grade. Quantitatively, both metabolite peak areas ratios of the resonances in the N-acetyl to choline regions, and choline to carbohydrate regions of the spectra are useful to discriminate discs of increasing Thompson grade with minimal overlap of individual ratios. Changes in $T_1$ and $T_2$ relaxation times of the chemical constituents of disc spectra do not mirror changes in water relaxation times previously reported for disc degeneration. Changes in relaxation times of the chemical constituents of disc spectra with increasing degeneration reflect both changes in dehydration of the disc and the degree of breakdown of the proteoglycan and collagen matrices with increasing Thompson grade. In vivo modalities of NMR spectroscopy will be useful for detecting chemical changes associated with disc degeneration.

In addition to the foregoing, the following references are herein incorporated in their entirety by reference thereto:
1. Haro H, Crawford, H. J. Clin. Invest. 2000; 105:143-150.
2. Mow V, Hayes, W. Basic Orthopaedic Biomechanics. In.: New York: Raven Press, 1991; 339-342.
3. Thompson J P, Pearce, R. H., Schechter, M. T., Adams, M. E., Tsang, I. K., Bishop, P. B. Preliminary evaluation of a scheme for grading the gross morphology of the human intervertebral disc. Spine 1990; 15:411-415.
4. Iatridis J C, Setton, L. A., Weidenbaum, M., Mow, V. C. Alterations in the mechanical behavior of the human lumbar nucleus pulposus with degeneration and aging. In: Journal of orthopaedic research, 1997; 318-322.
5. Urban J P, McMullin, J. F. Swelling pressure of the intervertebral disc: influence of proteoglycan and collagen contents. Biorheology 1985; 1985.
6. Beall P T, Amety, S. R. et al. States of Water in Biology: NMR Data Handbook for Biomedical Applications. New York: Pergamon Press, 1984.
7. Boos N, Boesch, C. Quantitative magnetic resonance imaging of the lumbar spine: potential for investigations of water content and biochemical composition. Spine 1995:2358-2366.
8. Bottomley P A, Foster, T. H. et al. A review of normal tissue hydrogen NMR relaxation times and relaxation mechanisms from 1-100 MHz: dependence on tissue type, NMR frequency, temperature, species, excision, and age. Medical Physics 1984:425-448.
9. Lyons G, Eisenstein, S. M. et al. Biochemical changes in intervertebral disc degeneration. Biochim Biophys Acta 1981:443-453.
10. Majors A W, McDevitt, C. A. et al. A correlative analysis of T2, ADC and MT ratios with water, hydroxyproline and GAG content in excised human intervertebral disk. In: 40th Annual Meeting Orthopaedic Research Society. New Orleans, La.: Orthopaedic Research Society, 1994.
11. Maroudas A. The Biology of the Intervertebral Disc. In: Ghosh P, ed. The Biology of the Intervertebral Disc. Boca Raton: CRC Press, 1988; Ch. 9.
12. Pearce R H, Grimmer, B. J. et al. Degeneration and the chemical composition of the human lumbar intervertebral disc. Journal of orthopaedic research 1987:198-205.
13. Tertti M, Paajanen, H. et al. Disc degeneration in magnetic resonance imaging: a comparative biochemical, histologic, and radiologic study in cadaver spines. Spine 1991:629-634.
14. Chui E, David C. Newitt, Mark R. Segal, Serena S. Hu, Jeffrey C. Lotz, Sharmila Majumdar. Magnetic Resonance Imaging Measurement of Relaxation and Water Diffusion in the Human Lumbar Intervertebral Disc Under Compression In Vitro. Spine 2001; 26:E437-444.
15. Gundry C R, Fritts, H. M. Magnetic resonance imaging of the musculoskeletal system: Part 8. The spine. Clin Orthop Rel Res 1997:275-287.
16. Gunzburg R P Rea. A cadaveric study comparing discography, magnetic resonance imaging, histology and mechanical behavior of the human lumbar disc. Spine 1991:417-423.
17. Modic M T, Pavlicek, W. et al. Magnetic resonance imaging of intervertebral disc disease: clinical and pulse sequence considerations. Radiology 1984:103-111.
18. Modic M T, Masaryk, T. J. et al. Lumbar herniated disk disease and canal stenosis: prospective evaluation by surface coil MR, CT and myelography. ANJR 1986:709-717.
19. Modic M T, Masaryk, T. J. et al. Imaging of degenerative disc disease. Radiology 1988:177-186.
20. Sether L A, Yu, S. et al. Intervertebral disk: Normal age-related changes in MR signal intensity. Radiology 1990:385-388.
21. Pfirrmann C, Metzdorf, A., Zanetti, M. Magnetic Resonance Classification of Lumbar Intervertebral Disc Degeneration. Spine 2001; 26:1873-1878.
22. Nieminen M T, Rieppo, J., Silvennoinen, J. et al. Spatial assessment of articular cartilage proteoglycans with Gd-DTPA-enhanced T1 imaging. Magnetic Resonance in Medicine 2002; 48:640-648.
23. Mosher T J, Dardzinski, B. J., Smith, M. B. Human articular cartilage: influence of aging and early symptomatic degeneration on the spatial variation of T2-preliminary findings at 3 T. Radiology 2000; 214:259-266.
24. Boos N, Wallin, A., Boesch, C. H., Aebi, M. Quantitative MR Imaging of diurnal water content variations in lumbar intervertebral disc. In: 38th Annual Meeting, Orthopeadic Research Society. Washington, D.C.: The Orthopaedic Research Society, 1992; 165.
25. Boos N, Wallin, A., Harms, S., Vock, P., Boesch, C. H., Aebi, M. Tissue characterization of normal and herniated lumbar intervertebral discs by quantitative MRI. In: 39th Annual Meeting, Orthopaedic Research Society. San Francisco, Calif.: Orthopaedic Research Society, 1993; 417.
26. Burstein D, Gray, M. L. et al. Diffusion of small solutes in cartilage as measured by nuclear magnetic resonance (NMR) spectroscopy and imaging. Journal of orthopaedic research 1993:465-478.
27. Koh K, Kusaka, Y. et al. Self diffusion coefficient of water and its anisotropic property in bovine intervertebral discs analyzed by pulsed gradient NMR method. Orthop Trans 1992:483.
28. Koh K, Kusaka, Y. et al. Self diffusion coefficient of water in human intervertebral discs analyzed by pulsed gradient NMR method. In: 39th Annual Meeting Orthopaedic Research Society. San Francisco, Calif., 1993.
29. Abdulkarim J A, Dhingsa, R., Finlay, D. B. Magnetic Resonance Imaging of the Cervical Spine: Frequency of Degenerative Changes in the Intervertebral Disc with Relation to Age. Clinical Radiology 2003:980-984.
30. Swanson M G, Vigneron D B, Tabatabai Z L, et al. Proton HR-MAS spectroscopy and quantitative pathologic analysis of MRI/3D-MRSI-targeted postsurgical prostate tissues. Magnetic Resonance in Medicine 2003; 50:944-954.
31. Schiller J, Naji, L., Huster, D., Kaufmann, J., Arnold, K. 1H and 13C HR-MAS NMR investigations on native and enzymatically digested bovine nasal cartilage. Magnetic Resonance Materials in Physics, Biology and Medicine 2001:19-27.

32. Carr H Y, Purcell, E. M. Effects of Diffusion on Free Precession in Nuclear Magnetic Resonance Experiments. Physical Review 1954; 94:630-638.
33. Kupce E. Applications of adiabatic pulses in biomolecular nuclear magnetic resonance. In: Methods in Enzymology, 2001; 82-111.
34. Mucci A, Schenetti, L., Volpi, N. 1H and 13C nuclear magnetic resonance identification and characterization of components of chondroitin sulfates of various origin. Carbohydrate Polymers 2000:37-45.
35. Goupille P, Jayson, M. I., Valat, J. P., Freemont, A. J. Matrix metalloproteinases: the clue to intervertebral disc degeneration? Spine 1998; 23:1612-1626.
36. Kang J D, Stefanovic-Racic, M., McIntyre, L. A., Georgescu, H. I., Evans, C. H. Toward a biochemical understanding of human intervertebral disc degeneration and herniation. Contributions of nitric oxide, interleukins, prostaglandin E2, and matrix metalloproteinases. Spine 1997; 22:1065-1073.
37. Weiler C, Nerlich, A. G., Zipperer, J., Bachmeier, B. E., Boos, N. 2002 SSE Award Competition in Basic Science: Expression of major matrix metalloproteinases is associated with intervertebral disc degradation and resorption. European Spine Journal 2002:308-320.
38. Urban J P, Roberts, S., Ralphs, J. R. The Nucleus of the Intervertebral Disc from Development to Degeneration. In: American Zoologist, 2000; 53-61.
39. Weidenbaum M, Foster, R. J., Best, B. A., Saed-Nejad, F., Nickoloff, E., Newhouse, J., Ratcliffe, A., Mow, V. C. Correlating magnetic resonance imaging with the biochemical content of the normal human intervertebral disc. Journal of orthopaedic research 1992; 10:552.

EXAMPLE 2

1. Introduction

Conventional imaging methods of assessing the painful, degenerated intervertebral disc generally focus solely on morphologic criteria. However, it is well-known that there is a poor correlation between morphologic findings and patient symptoms. The goal of this in vitro study is to utilize quantitative high-resolution magic angle spinning (HR-MAS) NMR spectroscopy as a tool to accurately characterize biochemical markers in disc specimens harvested from patients undergoing surgery. Spectra from discs obtained from patients that underwent discectomy for back pain and those of a reference population, consisting of patients undergoing surgery for scoliosis, were compared in attempts to identify biochemical signatures of painful disc degeneration.

2. Materials and Methods

Spectral data were acquired at 11.7T (500 MHz), 1° C., and a 2,250 Hz spin rate using a Varian INOVA spectrometer equipped with a 4 mm gHX nanoprobe. Disc tissue removed at surgery in patients with discogenic pain (n=6) and patients with scoliosis undergoing anterior and/or posterior spinal fusion (n=4) were studied using custom designed 35 ul rotors. Quantitative proton spectra were acquired for tissue samples (mean=14.28±2.91 mg) with D2O+0.75% TSP as a standard (Sigma-Aldrich, St. Louis, Mo.). A spin-echo rotor synchronized Carr-Purcell-Meiboom-Gill (CPMG) pulse sequence (nt=128, at=2.0 s, TR=5 s, echo time=80 ms) was acquired for each tissue sample. The lactate resonance (1.31 ppm, doublet), n-Acetyl resonance associated with proteoglycans (PG) (2.04 ppm, singlet), and collagen breakdown region (col) (3.30-4.00 ppm) were analyzed to compare disc specimens. These regions are annotated in further detailed spectra sections shown in FIGS. 7A and 7B.

3. Results

FIGS. 7A, 7B show representative 80 ms $^1$H CPMG spectra of (a) discogenic pain patient and (b) patient with scoliosis. The proteoglycan n-Acetyl resonance (PG) lactate, and collagen breakdown region (col) are indicated.

Relative to deformity patients, those with back pain demonstrate significantly lower PG/Lactate and PG/col ratios (p<0.05; see FIG. 7). In addition, Table 2 shows a table of information related to the experiment performed that produced the exemplary spectra shown in FIGS. 7A, 7B.

4. Discussion

The results from this experiment indicate that biochemical markers are useful to characterize processes that correlate with discogenic pain. Previous studies report the influence of pH on proteoglycan synthesis and overall health. As lactate concentrations increase, the effective pH of disc material decreases due to the increase in free H+ in solution, which can hinder proteoglycan synthesis.

The direct causal relationship between lactate concentration and pain is previously unknown or explained in fine biochemical detail here with respect to the present Experiment. However, the beneficial use of lactate concentration in providing a statistical correlation to pain is demonstrated according to the methods performed and summarized here. This presents a substantially useful tool in diagnosing locality of pain, regardless of mechanism of physical correlation between the two parameters. The highly beneficial systems and methods herein described provide distinct benefit in allowing a non-invasive tool to correlate measured factors to pain, regardless of the particular biological "cause-and-effect" chemical or biological relationships underlying these results. Nonetheless, it is believed that increased lactate may stimulate nerve fibers in granulation tissue associated with disc healing. Further studies with larger numbers of clinically-relevant samples that are matched for degeneration stage may be conducted by one of ordinary skill based upon a review of this disclosure and other available information, and to further confirm these and other areas of interest in identifying and using spectroscopic markers for assessing biochemical degeneration and association with discogenic pain.

The following documents are herein incorporated in their entirety by reference thereto:

Keshari K R, Zektzer A S, Swanson M G, Majumdar S, Lotz J C, Kurhanewicz J. Characterization of intervertebral disc degeneration by high-resolution magic angle spinning (HR-MAS) spectroscopy. Magn Reson Med 2005; 53(3): 519-527.

Maroudas A. The Biology of the Intervertebral Disc. In: Ghosh P, editor. The Biology of the Intervertebral Disc. Volume 2. Boca Raton: CRC Press; 1988. p Ch. 9.

Urban J P, Smith S, Fairbank J C. Nutrition of the intervertebral disc. Spine 2004; 29(23):2700-2709.

It is to be appreciated based upon the foregoing disclosure that NMR spectroscopy is useful to identify and characterize spinal disc material as to a corresponding degree of intervertebral disc degeneration, and in particular with direct and predictable, reproducible correlation to Thompson grades between discs. Accordingly, this represents one highly beneficial, and broad aspect of the present invention. One particular embodiment described in fine detail hereunder relates to use of high resolution magic angle spinning (HR-MAS) spectroscopy, shown in particular useful for explanted disc material observed in that diagnostic environment. However, other further, also highly beneficial embodiments also result, and represent further broad aspects disclosed hereunder, in regards to differentiating properties of living tissue in vivo. Such may be accomplished for example, either using other types of magic angle spinning systems specially adapted for use with living specimens, or by use of other NMR spectroscopy systems useful on patients and based upon suitably modified and adapted aspects and modes of the tools and methods taught hereunder.

By isolating high signal peaks for diagnostic pain correlation, as has been done here for example in Example 2 summarized above, such particular targets are considered to extend well from 11.7T MAS MRI tools and into equipment used directly with patients in clinical practice, e.g. 3 or 1.5T MRI equipment more typically used in clinical diagnosis. This may in particular be the case in the additional application of customized local coils for creating higher local fields along a region of interest, such as a particular region of lumbar spine for example.

Still further, it is to be appreciated that tissue samples may be taken from patients, such as through biopsies, and then run in laboratory equipment such as high field MRI machines, e.g. MAS NMR at 11.7T, for useful patient diagnosis according to the various systems and methods herein exemplified by way of the examples and description provided.

In addition, various exemplary chemicals and/or certain constituent factors thereof are herein described as targets of non-invasive diagnosis of medical conditions associated with tissues. It is appreciated that such chemical "factors" may include the identified chemical or molecular structure itself, or a portion thereof, or a metabolite, degradation product, or bi-product thereof to the extent correlative to the chemical identified. Moreover, the present disclosure deals with information that is produced by diagnostic tools and methods to indicate certain property(s) of tissue. Such property(s) may include for example pain or tissue degeneration themselves, respectively. Or, it may include another second property having correlation or causal link with such first property. For example, nociceptive nerves, related growth factors, certain types of inflammation, etc. may have causal links to either or both of pain and tissue degeneration. These may be the property directly indicated by the information produced by the present embodiments, whereas that indicated property further leads to additional useful diagnosis and conclusion as to the related pain or degeneration. It is also contemplated that pain and degeneration may be isolated results or targets of such diagnostic tools and methods herein described, and may furthermore be linked together in a combined result or target. Furthermore, degrees of such properties may be identified by the novel systems and methods herein described. This may lead to further results and conclusions as to spatial relationship of such property within a tissue, e.g. the location of a disc level, or portion of a disc (or other tissue structure), that is more painful or degenerated relative to other surrounding joints, levels, or areas of tissue. Such localization may be the nature of the useful information produced itself, or may be identified by further analysis and processing conducted upon the useful information produced.

EXAMPLE 3

1. Introduction

The goal of this study is to extend prior experience, using quantitative high-resolution magic angle spinning (HR-MAS) NMR spectroscopy to accurately characterize biochemical markers in disc specimens harvested from patients undergoing surgery, to experience observing NMR spectra of similar chemical signature targets in discs preserved in larger anatomic specimens using a commercially available clinical MRI system and commercially available surface coils. NMR spectroscopy data to be acquired and evaluated was for discs of ex-vivo bovine and cadaveric spines positioned in commercially available head coils, and discs of a living patient using a commercially available surface-spine coil. Papain was injected into bovine discs studied. This was intended to induce chemical degradation of proteoglycan, in order to monitor change over time in related magnetic resonance signals, in order to observe differences in the related NMR spectral peaks using the clinical test equipment and methods.

2. Materials and Methods

All MRI examinations were performed on a 3 Tesla (3T) GE Excite Signa whole-body MR scanner. Spine samples were acquired for evaluating target intervertebral discs in bovine (n=4) and cadaveric (n=4) ex-vivo studies. The ex-vivo studies used a GE 8-channel transmit/receive (T/R) phased array (PA) head coil or a GE 8-channel T/R PA knee coil. The in-vivo patient evaluation was done using a GE 6-channel spine coil. Single voxel spectroscopy imaging was conducted using a short-echo point-resolved spectroscopy (PRESS) sequence (TE/TR=35/2000 ms, 256 repetitions, 1024 data points), including chemical shift-selected (CHESS) water suppression. Data analysis included combining the data from multiple channels and calculating the ration of spectroscopy peak height of certain targets to be evaluated, namely N-Acetyl, Choline (Cho), and carbohydrate (carb), and additional data was evaluated for Lactate (Lac).

For the bovine disc portion of the study, the discs were scanned before Papain injection, 4 hours and 4-5 days after papain injection. The papain injection was made to achieve the enzymatic degradation of the nuclear pulpulsos. The solution was made by following the method described by Bradford (Spine 9:135-147).

Figure 21B:
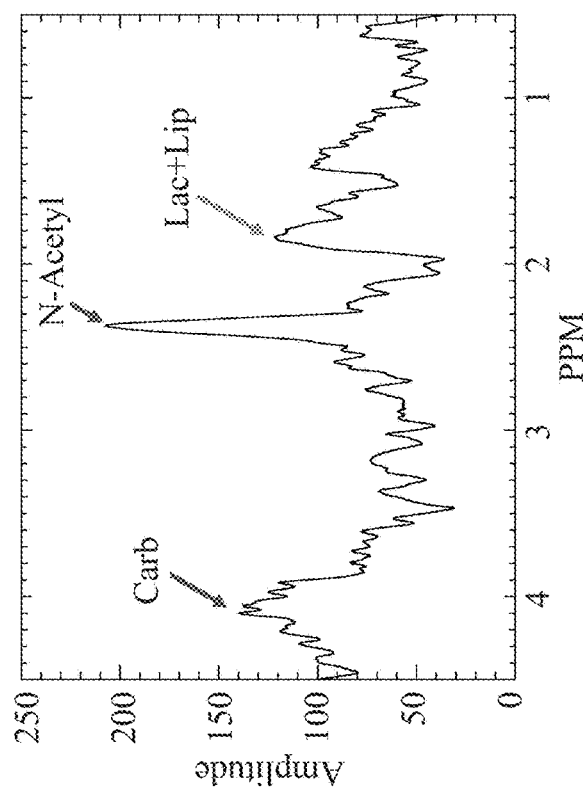
FIGS. 21A and 21B show a T2-weighted MRI image of a portion of a human patient's spine, and corresponding NMR spectrum of a voxel region in a disc nucleus of the spine, respectively, according to certain present embodiments.
Figure 21A:
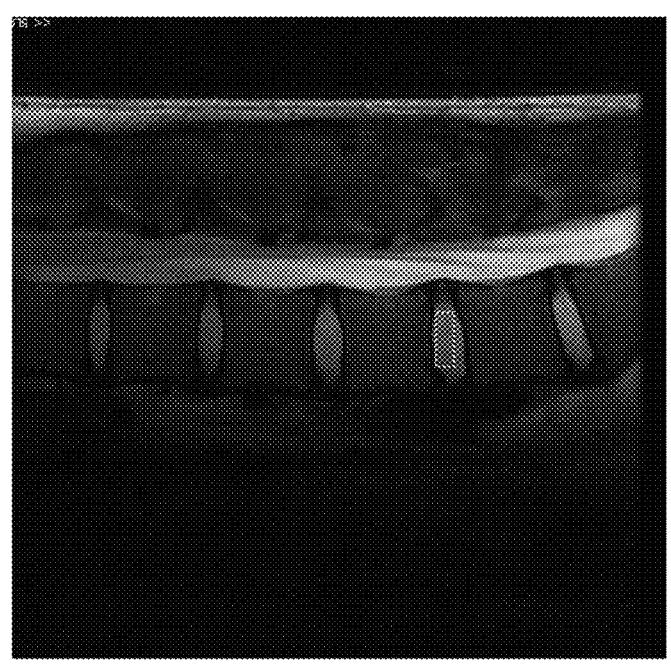

The disc regions evaluated in the study are shown via voxel box overlay on MRI images of: a first bovine disc in FIGS. 8A, 9A, 10A, and 11A, of a second bovine disc in FIGS. 12A, 13A, 14A, and 15A; five cadaveric discs in FIGS. 16A, 17A, 18A, 19A, and 20A; respectively, and in-vivo patient discs in FIG. 21A. NMR spectra corresponding with each of these images, annotating the target peak spectral sections used for spectral evaluation, are shown in following corresponding FIGS.: 8B, 9B, 10B, 11B, 12B, 13B, 14B, 15B, 16B, 17B, 18B, 19B, and 20B, respectively. Various Data Tables are provided for various peak ratios evaluated for the specimens in the study, as noted below.

3. Results

A. Ex-vivo Bovine Spine Study

For bovine disc #1 in the study, the T2-weighted images acquired at time intervals (a) before Papain injection, (b) 4 hours, (c) 24 hours, and (d) 4-5 days after papain injection, are shown in FIGS. 8A, 9A, 10A, and 11A, with single voxel overlay shown for disc nucleus region of the NMR spectral image taken. The corresponding spectroscopy images taken at these time intervals are shown in FIGS. 8B, 9B, 10B, and 11B, respectively, with respective target peak regions evaluated in data analysis indicated by arrows on overlay. As shown in Table 3, data analysis for bovine disc #1 demonstrated that N-Acetyl/cho ratio decreases with time and cho/carb composite ratio increases with time. Since papain injection is believed to cause disc degeneration, the results agree with prior results of previous experiments comparing non-degenerated vs. degenerated ex-vivo human disc tissue samples using HR-MAS.

For bovine disc #2 in the study, the T2-weighted images acquired at time intervals (a) before Papain injection, (b) 1-2 hours after injection, (c) 24 hours after injection, and (d) 4-5 days after injection, are shown in FIGS. 12A, 13A, 14A, and 15A, with single voxel overlay shown for disc nucleus region of the NMR spectral image taken. The corresponding spectroscopy images taken at these time intervals are shown in FIGS. 12B, 13B, 14B, and 15B, respectively, with respective target peak regions evaluated in data analysis indicated by arrows on overlay. The 1-2 hour time interval data was not included in analysis as it is unknown whether 1-2 hours is enough time for papain to have significant effect on the disc tissue structures under evaluation. As shown in Table 4 for this bovine disc #2 of the study, the N-Acetyl/cho ratio substantially decreases, and the cho/carb composite ratio substantially increases, over the time associated with tissue degeneration in the disc sample. This confirms the experience with bovine disc #1 in the study, and the prior experience of previous studies using similar peak ratio comparisons between non-degenerated and degenerated ex-vivo human disc tissue samples using HR-MAS spectroscopy.

For bovine disc samples #3 and #4, only tabular results are shown of the various spectral peak ratios, in Tables 5 and 6, respectively. For these discs, another time point of 2 days after papain injection was added to further evaluate the experimental papain effects. At this time point, changes in the spectral ratios are not substantial as longer time points. However, as of the 5 day time point, the N-Acetyl/cho and Cho/carb peak ratios for these bovine disc samples #3 and #4 are observed to undergo substantial changes similar to those observed for bovine disc samples #1 and 2 in the study.

B. Ex-vivo Cadaveric Spine Study

A cadaveric disc study was performed as follows. Five discs were targeted for use from five cadaveric spine samples. For the first cadaveric disc sample (reflected in T2-weighted image and single voxel spectral image in FIGS. 16A and B, respectively) this sample had a very low MRI signal and was excluded in the data analysis. Therefore, only the other four cadaveric discs intended for study were included in the analysis, indicated as cadaveric disc samples #1-4. T2-weighted images for these cadaveric discs #1-4 included in the analysis for this study are shown in FIGS. 17A, 18A, 19A, and 20A, with single voxel overlay shown for the disc nucleus region of NMR spectral image taken. The corresponding spectroscopy images taken at these time intervals are shown in FIGS. 17B, 18B, 19B, and 20B, respectively, with respective target peak regions evaluated in data analysis indicated by arrows on overlay. The number designation given to the test samples 1-4 were chosen in reverse order as to degree of their respective degradation as determined structurally per the T2-weighted MRI images (eg. Disc 1 being the most degraded, and Disc 4 being the least degraded in the sample population).

Table 7 shows similar spectral peak ratios analyzed for the cadaveric spine study as prior studies noted above. As indicated by bolded arrows in the first column, certain trends were apparent in each peak ratio presented between most to least degenerated discs per T2-weighted MRI image analysis. In particular, similar trends of N-Acetyl/cho and Cho/carb peak ratios were observed for the ex-vivo cadaver spine study as with prior bovine spine experience and prior HR-MAS disc tissue sample experience. More specifically, N-Acetyl/cho peak ratios were substantially lower, and below 1 indicating choline peak larger than N-Acetyl peak, for the more degradated Disc 1 and trending upward to N-Acetyl peak representing several multiple value to the choline peak for the most degradated Disc 4 among the samples. Similarly, the cho/carb peak ratios were substantially higher for the more degradated discs than the lower degradated discs, and in particular at the extremes comparing the respective data for Discs 1 and 4.

C. In vivo Human Patient Study

A healthy patient volunteer executed informed consent to NMR spectroscopy data acquisition for purposes of this study during an MRI scan taken of the patient's spine for other purposes. A T2-weighted image for the patient's spine is shown in FIG. 21A, with single voxel overlay shown for the disc nucleus region of NMR spectral image taken. The corresponding spectroscopy image is shown in FIG. 21B, with respective target peak regions evaluated in data analysis indicated by arrows on overlay. Based upon the T2-weighted image, and absence of clinical symptoms associated with degeneration or pain, the disc imaged is considered to be representative sample of a relatively normal, healthy disc.

Table 8 shows the similar peak spectral ratios for this in-vivo patient disc as those analyzed in prior studies noted above. As illustrated in the NMR spectrum shown in FIG. 21B, the single voxel region imaged in the disc nucleus (box overlay in FIG. 21A) did not appear to produce a representative choline (cho) peak in the NMR spectrum imaged for the region. Accordingly, as shown in Table 8, the N-Acetyl/cho peak ratio is shown as infinity, as the denominator is zero according to the absence of data in the NMR spectral data. Similarly, the cho/carb ratio is reflected in Table 8 as 0, again due to the absence of choline thus a zero value given to the absent peak.

The absence of choline is generally expected for typical normal healthy discs, as we have previously demonstrated that choline levels increase with disc degeneration. Choline is typically found in lipids that make up cell membranes and in the neurotransmitter acetylcholine. Consequently, the elevated choline levels noted in severely degenerated discs may represent increased cellularity associated with microvascularization and innervation, as compared with typical normal healthy discs. Thus, it is expected that a trend in NMR spectroscopy evaluation of normal healthy human discs should reveal the results reflected in the data shown for this pilot patient study. Based on our prior study with cadaveric tissues, there is an increasing presence of choline found in the NMR spectra imaged in increasingly degenerated discs, reflected in significantly decreased N-Acetyl/cho peak ratios and increased cho/carb peak ratios.

4. Discussion

The results from the study components included in this experiment confirm expected results of prior experiment conducted on non-degenerated and degenerated human disc tissue samples using HR-MAS spectroscopy. Trends in ratios between certain readily identifiable NMR spectral peaks known to represent N-Acetyl (generally associated with proteoglycan presence), choline (generally associated with cellularity), and carbohydrate, are confirmed to predictable outcomes in evaluating degeneration and as frequently associated with pain. The data analyzed in this study indicate that these peak ratios, and corresponding trends, can be readily evaluated using clinical MRI and local coil equipment. Each of four bovine spines evaluated in 3T MRI systems with local head and knee coils reflected similar identifiable changes in N-Acetyl/cho and cho/carb peaks under experimentally induced conditions believed to reasonably simulate general biochemical changes in the discs over a degenerative process. The one in-vivo human patient experience using a 3T MRI system and local spine coil reflected a predictable NMR spectral image of a normal healthy disc with respect to these particular peak ratios. This clinical experience confirms expected results from the prior ex-vivo experiments previously conducted.

5. Conclusion

The prior results analyzing NMR spectra of ex-vivo human spinal disc tissue samples using HR-MAS spectroscopy indicated that NMR spectral peak ratios associated with N-Acetyl/cho and cho/carb, and changes in those ratios, demonstrate repeatable and predictable characteristics between generally normal healthy discs and degenerated discs. Experiments conducted on whole bovine and cadaver spine specimens using clinical 3T MRI systems with commercially available local head and knee coils confirmed these prior results. This confirming experience in larger portions of anatomy (eg. whole preserved spine sections vs. excised disc tissue specimens) as test samples, using commercially available clinical MRI systems and local coils, further indicates clinical utility of imaging disc degradation and pain via the NMR spectroscopy analysis presented. Further in-vivo study conducted on one living human patient using a clinical 3T MRI system and local spine coil further confirmed NMR spectroscopy results of these peak ratios expected for normal healthy discs according to the prior experience in the previous ex-vivo studies, in particular in relation to N-Acetyl/cho and cho/carb peak ratios. Based upon this initial experience with one normal healthy human disc, an expected increase in choline from such normal healthy discs to degenerated discs would result in an expected decrease and increase, respectively, in these ratios. Simple further data acquisition and analysis from more patients with varying degrees of disc degradation per T2-weighted MRI may be readily performed and expected to confirm the expected trends and utility of such analysis in patient diagnosis and care. This further indicates that NMR spectroscopy conducted in the manner presented here has clinical utility in non-invasive imaging and evaluation of disc degeneration, including as is believed to be associated with pain. In particular, this study confirms clinical utility using non-invasive NMR spectroscopy with a commercially available clinical 3T MRI system and commercially available clinical spine coil for determining localized extent of disc degradation in a spine. In particular, the NMR spectral peak ratios of N-Acetyl/cho and cho/carb provide useful data in making this determination in what is believed to be a predictable, repeatable manner in a non-invasive clinical diagnostic setting.

It is further appreciated that certain surface coils were evaluated among the studies conducted, with confirming results. Examples include head, knee, and spine surface coils. It is further appreciated that more invasive approaches, such as for example probe-based coils, may provide still further benefit and utility when incorporated with the several aspects of the present disclosure, including for example enhanced resolution and spatial sensitivity with increased signal to noise ratios with respect to target NMR spectral features to be evaluated. For example, certain probe-based coils have been previously incorporated for prostate cancer evaluation in clinical MRI systems.

The present disclosure, to the extent directed toward specified systems and devices of the embodiments, further contemplates respective methods related thereto, whether or not such method(s) are specifically described in detail aside from their contemplated use in the system disclosure. One of ordinary skill will understand such relationship based upon the totality of the disclosure provided herein. Similarly, methods disclosed hereunder further contemplate respective system and device aspects clearly contemplated by such disclosure, whether or not specific reference to such system or device aspects is provided in particular aside from the method description. The foregoing relates to the description provided hereunder, as well as the claims provided below. For example but without limitation, it is to be appreciated that certain functional aspects (or interco-operation described between elements) of system or apparatus claims provided herewith further contemplate the methods of performing such function as additional, independent aspects contemplated hereunder, though not necessarily to be applied as limitations to the particularly specified aspects and related modes and embodiments unless described expressly so.

Although the description above contains many details, these should not be construed as limiting the scope of the invention but as merely providing illustrations of some of the presently preferred embodiments of this invention. Therefore, it will be appreciated that the scope of the present invention fully encompasses other embodiments which may become obvious to those skilled in the art, and that the scope of the present invention is accordingly to be limited by nothing other than the appended claims, in which reference to an element in the singular is not intended to mean "one and only one" unless explicitly so stated, but rather "one or more." All structural, chemical, and functional equivalents to the elements of the above-described preferred embodiment that are known to those of ordinary skill in the art are expressly incorporated herein by reference and are intended to be encompassed by the present claims. Moreover, it is not necessary for a device or method to address each and every problem sought to be solved by the present invention, for it to be encompassed by the present claims. Furthermore, no element, component, or method step in the present disclosure is intended to be dedicated to the public regardless of whether the element, component, or method step is explicitly recited in the claims. No claim element herein is to be construed under the provisions of 35 U.S.C. 112, sixth paragraph, unless the element is expressly recited using the phrase "means for."

TABLE 1A

| Disc Metabolite Ratios, Annulus Fibrosus | | | | | | |
|---|---|---|---|---|---|---|
| Integrated Areas | Grade 1 | Grade 3 | Grade 5 | 1 vs 3 | 1 vs 5 | 3 vs 5 |
| N-Acetyl/Cho | 3.685 ± 0.601 | 2.552 ± 0.339 | 1.941 ± 0.540 | 0.006 | 0.035 | 0.035 |
| Cho/Carb | 0.115 ± 0.027 | 0.191 ± 0.014 | 0.243 ± 0.016 | <0.001 | <0.001 | <0.001 |
| N-Acetyl/Carb | 0.420 ± 0.137 | 0.487 ± 0.062 | 0.466 ± 0.096 | 0.277 | 0.486 | 0.638 |

TABLE 1B

Disc Metabolite Ratios, Nucleus Pulposus

| Integrated Areas | Grade 1 | Grade 3 | Grade 5 | 1 vs 3 | 1 vs 5 | 3 vs 5 |
|---|---|---|---|---|---|---|
| N-Acetyl/Cho | 5.487 ± 1.400 | 4.336 ± 0.706 | 2.364 ± 0.411 | 0.031 | <0.001 | 0.001 |
| Cho/Carb | 0.082 ± 0.018 | 0.121 ± 0.014 | 0.161 ± 0.006 | 0.001 | <0.001 | 0.001 |
| N-Acetyl/Carb | 0.448 ± 0.139 | 0.515 ± 0.049 | 0.380 ± 0.079 | 0.465 | 0.146 | 0.006 |

TABLE 2

Ratios of PG/lactate, PG/Col, and Lactate/Col + 1 std deviation

|  | Disc Pain | Scoliosis |
|---|---|---|
| PG/Lactate | 0.37 ± 0.36 | 1.72 ± 0.81 |
| PG/col | 0.28 ± 0.14 | 0.66 ± 0.35 |
| Lactate/col | 0.70 ± 0.35 | 0.38 ± 0.08 |

TABLE 3

Ex-Vivo Bovine Disc #1; NMR Spectral Peak Ratios over time (Papain Injection)

| NMR Peak Ratios | Before Inject | 4 hrs after Inject | 24 hrs after Inject | 4 days after Inject |
|---|---|---|---|---|
| N-Acetyl/Lac +Lip ↓ | 4.88 | 2.52 | 2.65 | 1.64 |
| N-Acetyl/cho ↑ | 10.32 | 3.87 | 3.27 | 2.64 |
| Cho/carb | 0.31 | 0.43 | 0.53 | 0.82 |
| N-Acetyl/carb | 3.17 | 1.66 | 1.76 | 2.17 |

TABLE 4

Ex-Vivo Bovine Disc #2; NMR Spectral Peak Ratios over time (Papain Injection)

| NMR Peak Ratios | Before Inject | 1-2 hrs after Inject | 24 hrs after inject | 4 dys after inject |
|---|---|---|---|---|
| N-Acetyl/Lac + Li ↓ | 1.56 | 3.30 | 3.32 | 2.17 |
| N-Acetyl/cho ↑ | 7.65 | 7.69 | 3.10 | 2.90 |
| Cho/carb | 0.26 | 0.20 | 0.48 | 0.66 |
| N-Acetyl/carb | 1.97 | 1.56 | 1.48 | 1.91 |

TABLE 5

Ex-Vivo Bovine Disc #3; NMR Spectral Peak Ratios over time (Papain Injection)

| NMR Spectral Peak Ratios | before Injection | 24 hrs after Inject | 2 days after Inject | 5 days after Inject |
|---|---|---|---|---|
| N-Acetyl/Lac + Lip | 8.47 | 7.65 | 5.16 | 3.35 |
| N-Acetyl/cho ↓ | 4.23 | 3.31 | 4.13 | 2.05 |
| Cho/carb ↑ | 0.49 | 0.73 | 0.59 | 1.17 |
| N-Acetyl/carb | 2.07 | 2.42 | 2.45 | 2.40 |

TABLE 6

Ex-Vivo Bovine Disc #4; NMR Spectral Peak Ratios over time (Papain Injection)

| NMR Spectral Peak Ratios | Before Inject | 24 hrs after Inject | 2 days after Inject | 5 days after Inject |
|---|---|---|---|---|
| N-Acetyl/Lac + Lip | 2.38 | 2.26 | 3.66 | 4.25 |
| N-Acetyl/cho ↓ | 8.50 | 6.39 | 7.60 | 2.08 |
| Cho/carb ↑ | 0.17 | 0.54 | 0.33 | 0.77 |
| N-Acetyl/carb | 1.48 | 3.45 | 2.48 | 1.60 |

TABLE 7

Ex-Vivo Cadaver Discs #1-4; NMR Spectral Peak Ratios taken for Discs 1-4 (in reverse order of degree of degradation per structural analysis in T2-weighted MRI, eg. Disc 1 most degraded, Disc 4 least degraded); Arrows indicate trend in peak ratio values from Disc 1 to Disc 4.

| NMR Peak Ratios | Disc 1 | Disc 2 | Disc 3 | Disc 4 |
|---|---|---|---|---|
| N-Acetyl/Lac +Lip ↑ | 0.21 | 0.33 | 0.76 | 2.26 |
| N-Acetyl/cho* ↕ | 0.48 | 0.87 | 2.96 | 17.28 |
| Cho/carb* ↕ | 0.60 | 0.60 | 0.43 | 0.22 |
| N-Acetyl/carb ↑ | 0.28 | 0.52 | 1.27 | 3.88 |

TABLE 8

In-Vivo Human Patient Spine NMR Spectroscopy Study

| NMR Spectral Peak Ratios | Peak Ratio Values |
|---|---|
| N-Acetyl/Lac + Lip | 2.86 |
| N-Acetyl/cho | ∞ (expected to decrease w/ disc degeneration) |
| Cho/carb | 0 (expected to increase w/ disc degeneration) |

What is claimed is:

1. A medical diagnostic system for providing diagnostic information from a respective nuclear magnetic resonance (NMR) spectrum generated and acquired from each of a first region and a second region of tissue of a pain patient for determining if degenerative nociceptive pain is occurring in the respective regions, comprising:
an NMR spectroscopy system in a configuration that is operable to apply a magnetic pulse sequence to artificially induce NMR signals in each of the first and second regions, and to acquire said NMR signals, to thereby generate NMR spectroscopic data related to a respective NMR spectrum from each of the first region and second region and to provide the NMR spectroscopic data related to each respective NMR spectrum in a form that is processable, wherein the NMR spectroscopy system in the configuration comprises a local detector coil assembly in a configuration that is operable, in response to the applied magnetic pulse sequence, to acquire the NMR spectroscopic data from each of the respective first and second regions positioned in the NMR spectroscopy system;

a computer processor;

a non-transitory computer-readable memory storing instructions in the form of a computer readable software program executable by the computer processor to process the NMR spectroscopic data provided by the NMR spectroscopy system;

wherein said instructions, when executed by the computer processor, perform operations to:

determine first and second ratio values for the first and second regions, respectively, wherein each of the first and second ratio values is based at least in part on a ratio between spectral parameters associated with (a) an n-Acetyl-related resonance region of the respective NMR spectrum associated with chondroitin sulfate or a metabolite or degradation product thereof, and (b) a lactate-related resonance region of the respective NMR spectrum; and provide diagnostic information at least in part based upon said first and second ratio values, and wherein the diagnostic information corresponds with degenerative nociceptive pain.

2. The system of claim 1, wherein the computer program is further executable by the computer processor to process the NMR spectroscopic data to determine each respective ratio value based at least in part upon a measured feature of an n-Acetyl-realted resonance region of the respective NMR spectrum.

3. The system of claim 1, wherein the computer program is further executable by the computer processor to process the NMR spectroscopic data to determine the diagnostic information based at least in part upon a collagen-related factor.

4. The system of claim 1, wherein the computer program is further executable by the computer processor to process the NMR spectroscopic data to determine the diagnostic information based at least in part upon a measured feature of a choline-related region of the respective NMR spectrum.

5. The system of claim 1, wherein the computer program is further executable by the computer processor to process the NMR spectroscopic data to determine the diagnostic information based at least in part upon a measured feature of a carbohydrate-related region of the respective NMR spectrum.

6. The system of claim 1, wherein the computer program is further executable by the computer processor to process the NMR spectroscopic data to determine the diagnostic information based at least in part upon a measured feature of a region of the NMR spectrum associated with a collagen-related factor that comprises a chemical entity indicative of collagen break-down in the respective region.

7. The system of claim 1, wherein the computer program is further executable by the computer processor to process the NMR spectroscopic data to determine the diagnostic information based at least in part upon a first calculated ratio between a measured feature of the respective NMR spectrum associated with a proteoglycan-related factor and a measured feature of the NMR spectrum associated with a lactate-related factor, and a second ratio between a measured feature of the NMR spectrum associated with the proteoglycan-related factor and a measured feature of the NMR spectrum associated with a collagen-related factor in the respective region.

8. The system of claim 1, wherein the NMR spectroscopy system comprises a 3 Tesla NMR system.

9. The system of claim 1, wherein the NMR spectroscopy system in the configuration further comprises:

a first single voxel region prescribed to coincide with the first region of tissue in a first configuration;

wherein the NMR spectroscopy system is operable in the first configuration to apply the magnetic pulse sequence to induce a first NMR signal at the first single voxel region and acquire a first portion of the NMR spectroscopic data from the first single voxel region via the local detector coil assembly;

a second single voxel region prescribed to coincide with the second region of tissue in a second configuration;

wherein the NMR spectroscopy system is operable in the second configuration to apply the magnetic pulse sequence to induce a first NMR signal at the first single voxel region and acquire a second portion the NMR spectroscopic data from the second single voxel region via the local detector coil assembly.

10. The system of claim 1, wherein the at least one computer program is further executable by the computer processor to display a respective curve related to each respective NMR spectrum, and a portion of the curve comprises each said spectral parameter.

11. The system of claim 1, wherein:

respective spectral parameters of the lactate-related resonance region and the n-Acetyl-related resonance region correspond to a lactate-related chemical factor and a proteoglycan-related chemical factor, respectively, in each respective region; and wherein the ratio values comprise ratios between respective amounts of said chemical factors.

12. The system of claim 1, wherein said instructions, when executed by the computer processor, perform operations to compare the first and second ratio values, wherein the diagnostic information is based at least in part on the comparison of the first and second ratio values.

13. The system of claim 12, wherein the diagnostic information comprises a determination of where the degenerative nociceptive pain is being experienced between the first and second regions based at least in part on the comparison of the first and second ratio values.

14. A method for diagnosing whether local degenerative nociceptive pain is occurring in a first region of tissue versus a second region of tissue of a pain patient, comprising:

analyzing at least a lactate-related resonance region and a proteoglycan-related resonance region from nuclear magnetic resonance (NMR) spectroscopic data associated with a respective nuclear magnetic resonance (NMR) spectrum generated via acquired NMR signals induced in the first region via a magnetic pulse sequence applied via an NMR spectroscopy system, wherein the NMR spectroscopy system comprises a local detector coil assembly in a configuration that is operable, in response to the applied magnetic pulse sequence, to acquire the NMR signals and generate the spectroscopic data from the respective first region positioned in the NMR spectroscopy system;

producing a first ratio value from the analysis for the respective NMR spectrum from the first region and that indicates a ratio between spectral parameters associated with the lactate-related resonance region and the proteoglycan-related resonance region;

performing the analyzing and producing operations also for the second region of tissue of the patient positioned in the NMR spectroscopy system in order to produce a second ratio value for the second region;

comparing the first and second ratio values to determine where the local degenerative nociceptive pain is being experienced between the first and second regions based at least in part on the comparison of the first and second ratio values; and wherein the analyzing and the producing are performed by running a computer software program by a computer processor.

15. The method of claim 14, further comprising:

configuring an NMR spectroscopy system in a configuration that is operable to apply a magnetic pulse sequence to induce NMR signals, acquire the induced NMR signals, and generate and acquire the NMR spectroscopic data for the acquired NMR signals, from the first and second regions; and acquiring the NMR signals and generating the corresponding NMR spectroscopic data from the first and second regions by operating the NMR spectroscopy system in the configuration.

* * * * *